(12) United States Patent
Bose et al.

(10) Patent No.: US 7,668,292 B1
(45) Date of Patent: Feb. 23, 2010

(54) PATIENT SETUP ERROR EVALUATION AND ERROR MINIMIZING SETUP CORRECTION IN ASSOCIATION WITH RADIOTHERAPY TREATMENT

(75) Inventors: Supratik Bose, Walnut Creek, CA (US); Himanshu P. Shukla, Lafayette, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 12/198,645

(22) Filed: Aug. 26, 2008

(51) Int. Cl.
*A61N 5/10* (2006.01)
*G21K 5/08* (2006.01)

(52) U.S. Cl. .......................... 378/65; 378/68

(58) Field of Classification Search ............. 378/62–69, 378/207, 901
See application file for complete search history.

(56) References Cited

U.S. PATENT DOCUMENTS

| | | | | |
|---|---|---|---|---|
| 5,745,545 | A * | 4/1998 | Hughes | 378/65 |
| 5,815,547 | A * | 9/1998 | Shepherd et al. | 378/65 |
| 7,207,715 | B2 | 4/2007 | Yue | |
| 2005/0281374 | A1* | 12/2005 | Cheng et al. | 378/68 |
| 2008/0240350 | A1* | 10/2008 | Moyers | 378/65 |

OTHER PUBLICATIONS

Erik-Jan Rijkhorst et al., "Strategy for Online Correction of Rotational Organ Motion for Intensity-Modulated Radiotherapy of Prostate Cancer", Int. J. Radiation Oncology Biology Physics, vol. 69, No. 5, 2007, pp. 1608-1617, total 10 pages.

Ning J. Yue et al., "A method to implement full six-degree target shift corrections for rigid body in image-guided radiotherapy", Medical Physics, vol. 33, No. 1, Jan. 2006, © 2006 Am. Assoc. Phys. Med., pp. 21-31, total 11 pages.

Osamu Suzuki et al., "Novel correction methods as alternatives for the six-dimensional correction in CyberKnife treatment", Radiat Med. (2007) 25 pp. 31-37, total 7 pages.

Ludlum et al., "An algorithm for shifting MLC shapes to adjust for daily prostate movement during concurrent treatment with pelvic lymph nodes", Med Phys. Dec. 2007;34(12):4750-4756, total 7 pages.

* cited by examiner

*Primary Examiner*—Irakli Kiknadze

(57) ABSTRACT

In some embodiments, a method includes receiving, in a processor, information indicative of (i) a treatment plan defining planned treatment beams, (ii) a patient volume relative to a reference, (iii) ideal intersections of the planned treatment beams with the patient volume at the time the patient is to be treated, (iv) any constraints that prevent achievement of the recommended repositioning using only the patient support, (v) an allowable change to a gantry position from a planned value and an allowable change to a collimator position from a planned value; defining, in the processor, a plurality of alternatives based at least in part on the information indicative of any constraints of the patient support and the information indicative of allowable movement of the gantry and collimator, each alternative defining a modified patient support position and modified beams, each modified beam being based at least in part on a respective one of the planned treatment beams, the change to the position of the gantry for the respective planned treatment beam and the change to the position of the collimator for the respective planned treatment beam; determining, in the processor, for each modified beam of each alternative, an intersection of the patient volume and the modified beam, with the patient volume positioned on the patient support and the patient support having the modified patient support position defined by the alternative; and defining, in the processor, for each alternative, a measure of difference between the ideal intersections and the intersections for the modified beams of the alternative.

33 Claims, 15 Drawing Sheets

700

702 DEFINING, FOR EACH MODIFIED BEAM OF THE ALTERNATIVE, A MEASURE OF DIFFERENCE BETWEEN THE INTERSECTION AND A RESPECTIVE ONE OF THE IDEAL INTERSECTIONS

704 DEFINING A MEASURE OF DIFFERENCE BETWEEN THE IDEAL INTERSECTIONS AND THE INTERSECTIONS FOR THE MODIFIED BEAMS OF THE ALTERNATIVE BASED AT LEAST IN PART ON THE MEASURE OF DIFFERENCE BETWEEN THE INTERSECTION AND THE RESPECTIVE ONE OF THE IDEAL INTERSECTIONS FOR EACH MODIFIED BEAM OF THE ALTERNATIVE

FIG. 7

800

```
┌─────────────────────────────────────────────┐
│ DEFINING EACH INTERSECTION AS A PYRAMID     │
│ HAVING A TIP AND A POLYGONAL BASE           │
│                                         802 │
└─────────────────────────────────────────────┘
                      ↓
┌─────────────────────────────────────────────┐
│ DEFINING A DISTANCE BETWEEN THE TIP OF THE  │
│ INTERSECTION FOR THE MODIFIED BEAM AND THE  │
│ TIP OF THE RESPECTIVE IDEAL INTERSECTION 804│
└─────────────────────────────────────────────┘
                      ↓
┌─────────────────────────────────────────────┐
│ DEFINING FOR EACH CORNER OF THE POLYGONAL   │
│ BASE, A DISTANCE BETWEEN THE CORNER AND A   │
│ CORRESPONDING CORNER OF THE RESPECTIVE IDEAL│
│ INTERSECTION                            806 │
└─────────────────────────────────────────────┘
                      ↓
┌─────────────────────────────────────────────┐
│ DEFINING A SQUARE OF THE DISTANCE BETWEEN   │
│ THE TIPS                                808 │
└─────────────────────────────────────────────┘
                      ↓
┌─────────────────────────────────────────────┐
│ DEFINING A SQUARE OF THE DISTANCE DEFINED   │
│ FOR EACH CORNER                         810 │
└─────────────────────────────────────────────┘
                      ↓
┌─────────────────────────────────────────────┐
│ DEFINING THE MEASURE OF DIFFERENCE BETWEEN  │
│ AN INTERSECTION AND THE RESPECTIVE IDEAL    │
│ INTERSECTION BASED AT LEAST IN PART ON A    │
│ SUM OF THE SQUARE OF THE DISTANCE BETWEEN   │
│ THE TIPS AND THE SQUARE OF THE DISTANCE     │
│ DEFINED FOR EACH CORNER OF THE POLYGON  812 │
└─────────────────────────────────────────────┘
                      ↓
```

FIG. 8

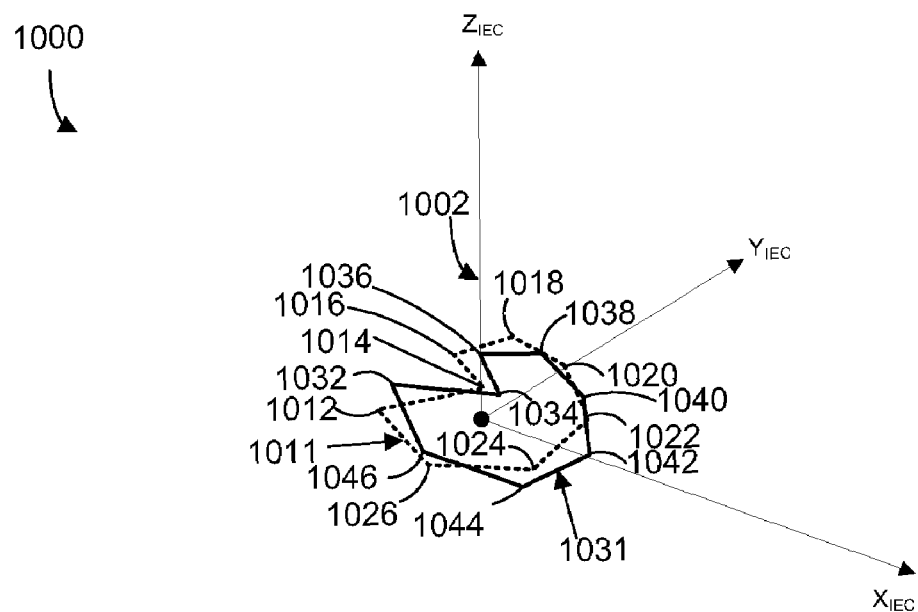
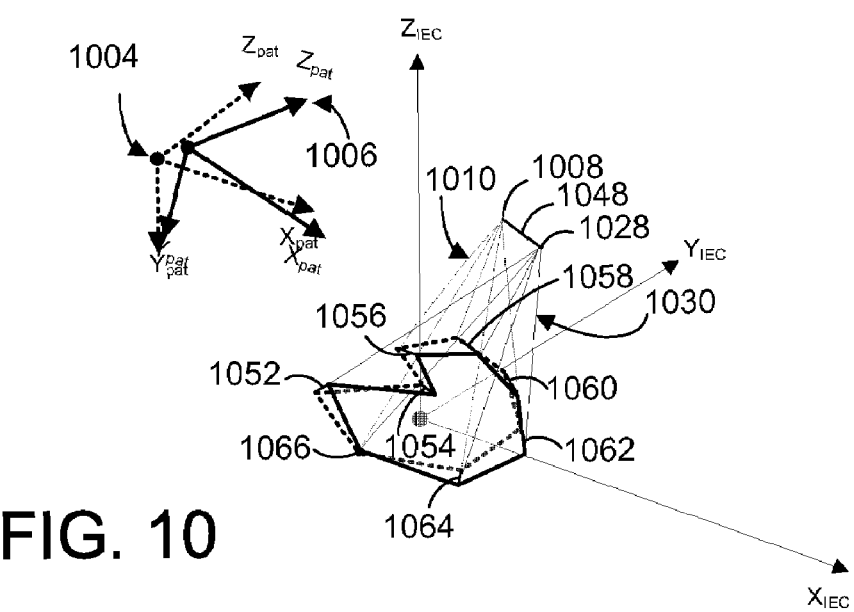
FIG. 10

| | BEAM NO. | Change Support POS. X-AXIS | Change Support POS. Y-AXIS | Change Support POS Z-AXIS. | Change Support POS. DEG. | Change GANTRY POS. | Change COLL. POS. |
|---|---|---|---|---|---|---|---|
| 1101 | 1 | 0 | 0 | 0 | 0 | 0 | 0 |
| | 2 | 0 | 0 | 0 | 0 | 0 | 0 |
| | 3 | 0 | 0 | 0 | 0 | 0 | 0 |
| | 4 | 0 | 0 | 0 | 0 | 0 | 0 |
| 1102 | 1 | 0 | 0 | 0 | 0 | 0 | +1 |
| | 2 | 0 | 0 | 0 | 0 | 0 | 0 |
| | 3 | 0 | 0 | 0 | 0 | 0 | 0 |
| | 4 | 0 | 0 | 0 | 0 | 0 | 0 |
| 1103 | 1 | 0 | 0 | 0 | 0 | 0 | 0 |
| | 2 | 0 | 0 | 0 | 0 | 0 | +1 |
| | 3 | 0 | 0 | 0 | 0 | 0 | 0 |
| | 4 | 0 | 0 | 0 | 0 | 0 | 0 |
| ⋮ | ⋮ | ⋮ | ⋮ | ⋮ | ⋮ | ⋮ | ⋮ |
| 1104 | 1 | 0 | 0 | 0 | 0 | 0 | +5 |
| | 2 | 0 | 0 | 0 | 0 | 0 | +5 |
| | 3 | 0 | 0 | 0 | 0 | 0 | +5 |
| | 4 | 0 | 0 | 0 | 0 | 0 | +5 |
| 1105 | 1 | 0 | 0 | 0 | 0 | +1 | 0 |
| | 2 | 0 | 0 | 0 | 0 | 0 | 0 |
| | 3 | 0 | 0 | 0 | 0 | 0 | 0 |
| | 4 | 0 | 0 | 0 | 0 | 0 | 0 |
| ⋮ | ⋮ | ⋮ | ⋮ | ⋮ | ⋮ | ⋮ | ⋮ |
| 1106 | 1 | +5 | +5 | +5 | +5 | +5 | +4 |
| | 2 | +5 | +5 | +5 | +5 | +5 | +5 |
| | 3 | +5 | +5 | +5 | +5 | +5 | +5 |
| | 4 | +5 | +5 | +5 | +5 | +5 | +5 |
| 1107 | 1 | +5 | +5 | +5 | +5 | +5 | +5 |
| | 2 | +5 | +5 | +5 | +5 | +5 | +5 |
| | 3 | +5 | +5 | +5 | +5 | +5 | +5 |
| | 4 | +5 | +5 | +5 | +5 | +5 | +5 |

FIG. 11

PATIENT SETUP ERROR EVALUATION AND ERROR MINIMIZING SETUP CORRECTION IN ASSOCIATION WITH RADIOTHERAPY TREATMENT

BACKGROUND

1. Field

Some embodiments described herein relate generally to radiation treatment, and more particularly, to methods, apparatus and computer readable mediums for use in accounting, at least in part, for changes in a position of a tumor or other target volume within a patient.

2. Description

According to conventional radiation therapy, a beam of radiation is directed toward a tumor located within a patient. The radiation beam delivers a predetermined dose of therapeutic radiation to the tumor according to an treatment plan. The delivered radiation kills cells of the tumor by causing ionizations within the cells.

Recent advances in fractionated external beam radiation therapy, such as three-dimensional conformal and intensity-modulated radiation therapy (IMRT), have increased the ability to deliver radiation doses that conform tightly to a target volume. This tight conformance results in steep dose gradients inside the volume. For example, IMRT can create a dose gradient of 10% $mm^{-1}$ inside a target volume.

A treatment plan is designed assuming that a target volume will be in a particular position relative to a beam source during treatment. If the target volume is not positioned exactly as assumed by the treatment plan, the steep gradient may occur within sensitive healthy tissue surrounding the volume causing destruction of healthy tissue while sparing some malignant tissue. Thus, it is increasingly important to precisely position the target volume with respect to the beam source.

It is not unusual for the target volume to change position within the patient (e.g., to translate along one or more axes and/or rotate about one or more axes) after a treatment plan is designed but prior to performing the treatment.

In order to know current location of the target volume with respect to the external beams, three-dimensional imaging of the patient is often provided immediately prior to treatment delivery (i.e., when the patient is on the treatment table). Systems attempting to provide such imaging include: (1) a "CT on rails" system, requiring an additional diagnostic computed tomography machine in the treatment room; (2) a kilovoltage cone beam CT (kVCBCT) system, consisting of an additional kilovoltage X-ray source and detector attached to a treatment gantry; (3) a megavoltage cone beam CT (MVCBCT) system using the pre-existing treatment machine and an EPID for imaging; (4) a MVCT system, using the pre-existing treatment machine with an attached arc of detectors; (5) a tomotherapy system, replacing the traditional treatment machine with a CT ring and a MV beam source; and (6) a pre-treatment magnetic resonance imaging (MRI) of the patient.

From pre-treatment imaging, a shift of the target volume with respect to the external beams can be found and the patient position is adjusted in order to position the tumor targets in the intended planned position with respect to the external beams. Typically, the shift of such target volumes can be modeled as rigid body rotation around along three orthogonal axis and rigid body translation along three orthogonal axis. Adjustments of the patient position typically involve movement of a radiotherapy couch.

For example, if the treatment system uses a robotic couch having six degrees of freedom (e.g., translation along three axes and rotation about three axes), the patient may be placed on the robotic couch and the couch may be actuated so as to move the patient to a position at which the tumor has a position, relative to the treatment system, that is the same as that used in defining the radiation treatment plan.

If the treatment system uses a table having only four degrees of freedom (e.g., translation along three axes and rotation about one axis), the positions of the table, the gantry and the collimator may be each adjusted for each planned beam, such that the tumor, the gantry and the collimator have the same relative positioning as defined by the treatment plan. (See Yue et al., A method to implement full six-degree target shift corrections for rigid body in image-guided radiotherapy. Medical Physics, 33(1):21-31, January 2006.)

Alternately, without moving a treatment couch, the collimator may be rotated and leaves and jaws of the collimator for a beam may be repositioned to match a current position and shape of the target volume with respect to the beam and the dose is then recomputed. (See Ludlum et al., An algorithm for shifting MLC shapes to adjust for daily prostate movement during concurrent treatment with pelvic lymph nodes, Med Phys. 2007 December; 34(12):4750-6. See also Erik-Jan Rijkhorst et al. Strategy for online correction of rotational organ motion for intensity-modulated radiotherapy of prostate cancer. International Journal of Radiation Oncology*Biology*Physics, 69:1608-1617, 2007).

SUMMARY

A disadvantage of the above method described in Yue et al. for systems that use a table having only four degrees of freedom is that the table position must be changed for each beam. This can have the effect of increasing the time needed to perform the treatment. Moreover, in some embodiments, any change to the position of the treatment table has the potential to disturb the position of the patient relative to the table.

A disadvantage of the above method described in Ludlum et al. is that the dose must be recomputed, which can be time consuming.

Some embodiments described herein provide a method, an apparatus, and/or an article for use in association with radiation treatment, and more particularly, for use in accounting, at least in part, for changes in a position of a tumor or other target volume within a patient.

Some embodiments described herein overcome one or more of the disadvantages described above.

In one aspect, a method includes: receiving, in a processor, information indicative of (i) a treatment plan defining planned treatment beams, (ii) a patient volume relative to a reference, (iii) ideal intersections of the planned treatment beams with the patient volume at the time the patient is to be treated, (iv) any constraints that prevent achievement of the recommended repositioning using only the patient support, (v) an allowable change to a gantry position from a planned value and an allowable change to a collimator position from a planned value; defining, in the processor, a plurality of alternatives based at least in part on the information indicative of any constraints of the patient support and the information indicative of allowable movement of the gantry and collimator, each alternative defining a modified patient support position and modified beams, each modified beam being based at least in part on a respective one of the planned treatment beams, a change to the position of the gantry for the respective planned treatment beam and a change to the position of the collimator for the respective planned treatment beam; determining, in the processor, for each modified beam of each alternative, an intersection of the patient volume and the modified beam, with the patient volume positioned on the patient support and the patient support having the modified patient support position defined by the alternative; and defining, in the processor, for each alternative, a measure of difference between the ideal intersections and the intersections for the modified beams of the alternative.

In one aspect, an apparatus includes a processor to: receive information indicative of (i) a treatment plan defining planned treatment beams, (ii) a patient volume relative to a reference, (iii) ideal intersections of the planned treatment beams with the patient volume at the time the patient is to be treated, (iv) any constraints that prevent achievement of the recommended repositioning using only the patient support, (v) an allowable change to a gantry position from a planned value and an allowable change to a collimator position from a planned value; define a plurality of alternatives based at least in part on the information indicative of any constraints of the patient support and the information indicative of allowable movement of the gantry and collimator, each alternative defining a modified patient support position and modified beams, each modified beam being based at least in part on a respective one of the planned treatment beams, a change to the position of the gantry for the respective planned treatment beam and a change to the position of the collimator for the respective planned treatment beam; determine for each modified beam of each alternative, an intersection of the patient volume and the modified beam, with the patient volume positioned on the patient support and the patient support having the modified patient support position defined by the alternative; and define for each alternative, a measure of difference between the ideal intersections and the intersections for the modified beams of the alternative.

In one aspect, an article includes: a processor readable storage medium having stored thereon instructions that if executed by a processor, result in the following: receiving information indicative of (i) a treatment plan defining planned treatment beams, (ii) a patient volume relative to a reference, (iii) ideal intersections of the planned treatment beams with the patient volume at the time the patient is to be treated, (iv) any constraints that prevent achievement of the recommended repositioning using only the patient support, (v) an allowable change to a gantry position from a planned value and an allowable change to a collimator position from a planned value; defining a plurality of alternatives based at least in part on the information indicative of any constraints of the patient support and the information indicative of allowable movement of the gantry and collimator, each alternative defining a modified patient support position and modified beams, each modified beam being based at least in part on a respective one of the planned treatment beams, a change to the position of the gantry for the respective planned treatment beam and a change to the position of the collimator for the respective planned treatment beam; determining for each modified beam of each alternative, an intersection of the patient volume and the modified beam, with the patient volume positioned on the patient support and the patient support having the modified patient support position defined by the alternative; and defining for each alternative, a measure of difference between the ideal intersections and the intersections for the modified beams of the alternative.

In some embodiments, each alternative comprises a potential setup correction that involves a one-time movement (translation and/or vertical rotation) of the patient support and planned-beam-specific modification of gantry and collimator angle.

Some embodiments select an alternative having a minimum difference with respect to the ideal intersections to compensate, at least in part, for a six-degree of movement of the tumor or other target volume within the patient.

In some embodiments, each treatment segment of each radiotherapy beam emanates from a beam limiting device and produces a pyramidal shaped intersection with the patient volume. In some embodiments, the pyramidal shape has a polygonal shaped base at an isocentric plane.

In some embodiments, a measure of geometric error is used to compute the difference between each possible set-up correction and the ideal setup correction.

In some embodiments, the measure of geometric error is based on the Euclidean distance between corresponding points of the pyramidal intersections generated by the proposed and ideal pyramidal intersections. In some embodiments, the measure of geometric error is based on the Euclidean distance between tips of the pyramidal intersections generated by the proposed and ideal pyramidal intersections and on the Euclidean distance between corresponding corner points of the polygonal shaped base of the pyramidal intersections generated by the proposed and ideal pyramidal intersections.

In some embodiments, the geometric error for a treatment segment may be weighted by the intended dose to be delivered by the segment.

In some embodiments, an alternative that produces the least dose-weighted geometric error, is obtained using an optimization procedure.

In some embodiments, the modified patient support position defined by each alternative is the same.

In some embodiments, the amount of change to the gantry position defined by each alternative is the same.

In some embodiments, the amount of change to the collimator position defined by each alternative is the same.

Some embodiments, define, for each modified beam of the alternative, a measure of difference between the intersection and a respective one of the ideal intersections, and define the measure of difference between the ideal intersections and the intersections for the modified beams based at least in part on the measure of difference between the intersection and the respective one of the ideal intersections for each modified beam of the alternative.

In some embodiments, the measure of difference between each intersection and the respective ideal intersection is based at least in part on a distance between a point defined by the intersection and a corresponding point defined by the respective ideal intersection.

In some embodiments, each intersection for a modified beam defines a pyramid having a tip and a polygonal base, the tip defined by a source for the modified beam, the polygonal base having a plurality of corners.

Some embodiments define a distance between the tip of the intersection and a tip of the respective ideal intersection; further define a square of the distance between the tips; further define for each corner of the polygonal base of the intersection, a distance between the corner and a corresponding corner of the respective ideal intersection; further define a square of the distance for each corner; and further define the measure of difference based at least in part on a sum of the square of the distance between the tips and the square of the distance defined for each corner of the polygon.

Some embodiments define, for each modified beam of the alternative, a measure of difference between the intersection and a respective one of the ideal intersections; further define, for each modified beam of the alternative, a weighted difference defined as a product of a weight and the measure of difference between the intersection and a respective one of the ideal intersections, wherein the weight is based at least in part on a dosimetric strength of the modified beam relative to respective dosimetric strengths of the other modified beams of the alternative; and further define the measure of difference between the ideal intersections and the intersections for the modified beams based at least in part on the weighted difference for each modified beam of the alternative.

In some embodiments, the measure of difference between the ideal intersections and the intersections for the modified beams is based at least in part on the sum of the weighted difference for each modified beam of the alternative.

Some embodiments select one alternative of the plurality of alternatives based at least in part on the measure of difference for the one alternative.

Some embodiments select one alternative of the plurality of alternatives for which the measure of difference between the ideal intersections and the intersections for the modified beams of the alternative is no greater than the measure of difference between the ideal intersections and the intersections for the modified beams of the other alternatives.

One or more of the alternatives may avoid change to the position of the patient support. This may help reduce the potential to disturb the position of the patient relative to the patient support.

Although various features, attributes and/or advantages may be described and/or may be apparent in light of the description, it should be understood that unless stated otherwise, such features, attributes and/or advantages are not required and need not be present in all aspects and/or embodiments.

BRIEF DESCRIPTION OF THE DRAWINGS

Various embodiments will be apparent from the following detailed description and accompanying drawings, in which like reference numerals designate like parts, and wherein:

FIG. 7 is a flow diagram of a process according to some embodiments;

FIG. 8 is a flow diagram of a process according to some embodiments;

FIG. 10 is a diagrammatic representation of an ideal intersection and a modified intersection, according to some embodiments;

FIG. 11 is a table of a subset of alternatives within a search space, in accordance with some embodiments, is described below with respect to FIG. 11.

DETAILED DESCRIPTION

Figure 1:
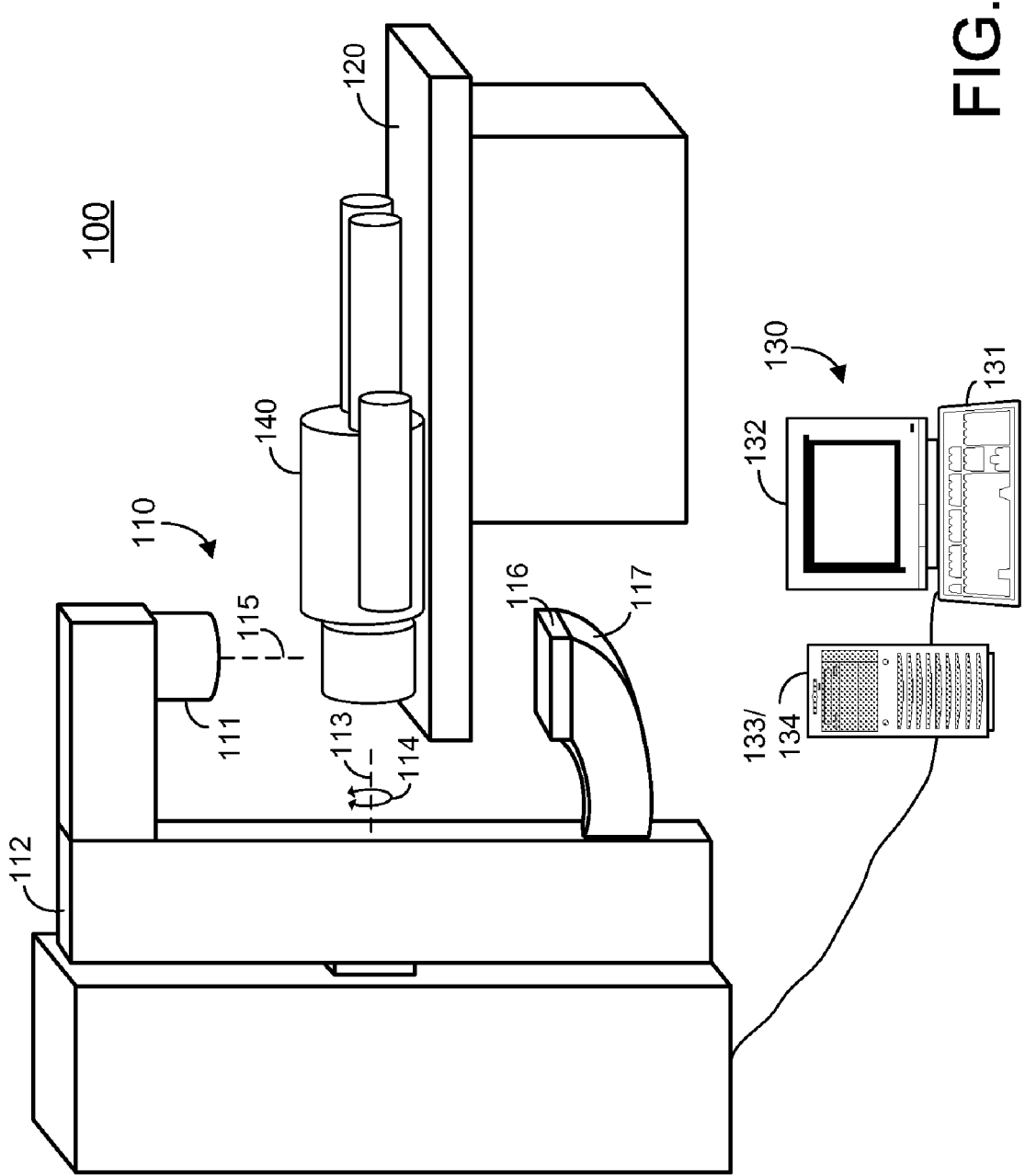
FIG. 1 is a perspective view of a radiation treatment room according to some embodiments.

FIG. 1 is a perspective view of a radiation treatment room 100 according to some embodiments. In accordance with some embodiments, radiation treatment room 100 includes linear accelerator (linac) 110, patient support 120 and operator console 130. The elements of radiation treatment room 100 may be used to deliver radiation to a target volume of beam object 140. In this regard, beam object 140 may comprise a patient positioned to receive radiation according to a radiation treatment plan. The elements of treatment room 100 may be employed in other applications according to some embodiments.

Linac 110 generates and emits the radiation, and is primarily composed of treatment head 111 and gantry 112. Treatment head 111 includes a beam-emitting device (not shown) for emitting a radiation beam used during calibration, verification, and/or treatment. The radiation beam may comprise electron, photon or any other type of radiation. According to some embodiments, the radiation beam exhibits energies in the megavoltage range (i.e. >1 MeV) and may therefore be referred to as megavoltage radiation.

Treatment head 111 is coupled to a projection of gantry 112. Gantry 112 is rotatable around gantry axis 113 before, during and after radiation treatment. As indicated by arrow 114, gantry 112 may rotate clockwise or counter-clockwise according to some embodiments. Rotation of gantry 112 serves to rotate treatment head 111 around axis 113.

Also included within treatment head 111 is a beam-shielding device, or collimator 200 (FIG. 2) for shaping the beam and for shielding sensitive surfaces from the beam.

During radiation treatment, a radiation beam is emitted from treatment head 111 as a divergent beam. The beam is emitted towards an isocenter of linac 110. The isocenter is located at the intersection of beam axis 115 and gantry axis 113. Due to divergence of the radiation beam and the shaping of the beam by the aforementioned beam-shaping devices, the beam may deliver radiation to a volume of beam object 140 rather than only to the isocenter.

The patient support 120 supports beam object 140 during radiation treatment. The table patient support 120 may be adjustable to assist in positioning a treatment area of beam object 140 at the isocenter of linac 110. The patient support 120 may also be used to support devices used for such positioning, for calibration and/or for verification.

In some embodiments, the patient support 120 comprises a table (sometimes referred to herein as a treatment or radiotherapy table), a couch (sometimes referred to herein as a treatment or radiotherapy couch) and/or any other type of structure(s) or combination thereof.

Imaging device 116 may acquire images before, during and/or after radiation treatment. For example, imaging device 116 may be used to acquire images for verification and recordation of a target volume position and of an internal patient portal to which radiation is delivered and/or to be delivered.

In some embodiments, imaging device 116 may be attached to gantry 112, for example, via extendible and retractable housing 117. Rotation of gantry 112 may cause treatment head 111 and imaging device 116 to rotate around the isocenter such that isocenter remains located between treatment head 111 and imaging device 116 during the rotation.

In some embodiments, linac 110 is capable of producing kilovoltage photon radiation via beamline modification or other techniques, and imaging device 116 may acquire images based on such kilovoltage radiation. In some embodiments, imaging device 116 comprises a system to acquire an image based on received megavoltage photon radiation.

In some embodiments, imaging device 116 is a flat-panel imaging device using a scintillator layer and solid-state amorphous silicon photodiodes deployed in a two-dimensional array. In operation, the scintillator layer receives photons and generates light in proportion to the intensity of the received photons. The array of photodiodes receives the light and records the intensity of received light as stored electrical charge.

In other embodiments, imaging device 116 converts received photons to electrical charge without requiring a scintillator layer. The photons are absorbed directly by an array of amorphous selenium photoconductors. The photoconductors convert the photons directly to stored electrical charge. Imaging device 116 may also comprise a CCD or tube-based camera. Such an imaging device may include a light-proof housing within which are disposed a scintillator, a mirror, and a camera.

The charge developed and stored by imaging device 116 represents radiation intensities at each location of a radiation field produced by a beam emitted from treatment head 111. Since object 140 is located between treatment head and imaging device 116, the radiation intensity at a particular location represents the attenuative properties of tissues along a divergent line between a radiation source in treatment head 111 and the particular location. The set of radiation intensities acquired by imaging device 116 may therefore comprise a two-dimensional projection image of these tissues.

Operator console 130 includes input device 131 for receiving instructions from an operator and output device 132, which may be a monitor for presenting operational parameters of linac 110 and imaging device 116 and/or interfaces for receiving instructions. Output device 132 may also present a two-dimensional projection image, a three-dimensional megavoltage (or kilovoltage) cone beam image and/or two-dimensional "slice" images based on the three-dimensional image.

Input device 131 and output device 132 are coupled to processor 133 and storage 134. Processor 133 may execute program code to perform any of the determinations and generations described herein, and/or to cause linac 110 to perform one or more portions of a treatment plan.

Storage 134 may store program code to generate and/or modify a treatment plan according to some embodiments. Such code may comprise the COHERENCE™ workspace or the KONRAD™ treatment planning system sold by Siemens Medical Solutions. Accordingly, storage 134 may also store radiation treatment plans in accordance with any currently- or hereafter-known format. The treatment plans may comprise scripts that are automatically executable by elements of room 100 to provide radiation therapy fractions. Each fraction of each treatment plan may require a patient to be positioned in a particular manner with respect to treatment head 111.

Operator console 130 may be in a room other than treatment room 100, in order to protect its operator from radiation. For example, treatment room 100 may be heavily shielded, such as a concrete vault, to shield the operator from radiation generated by linac 110.

Figure 2:
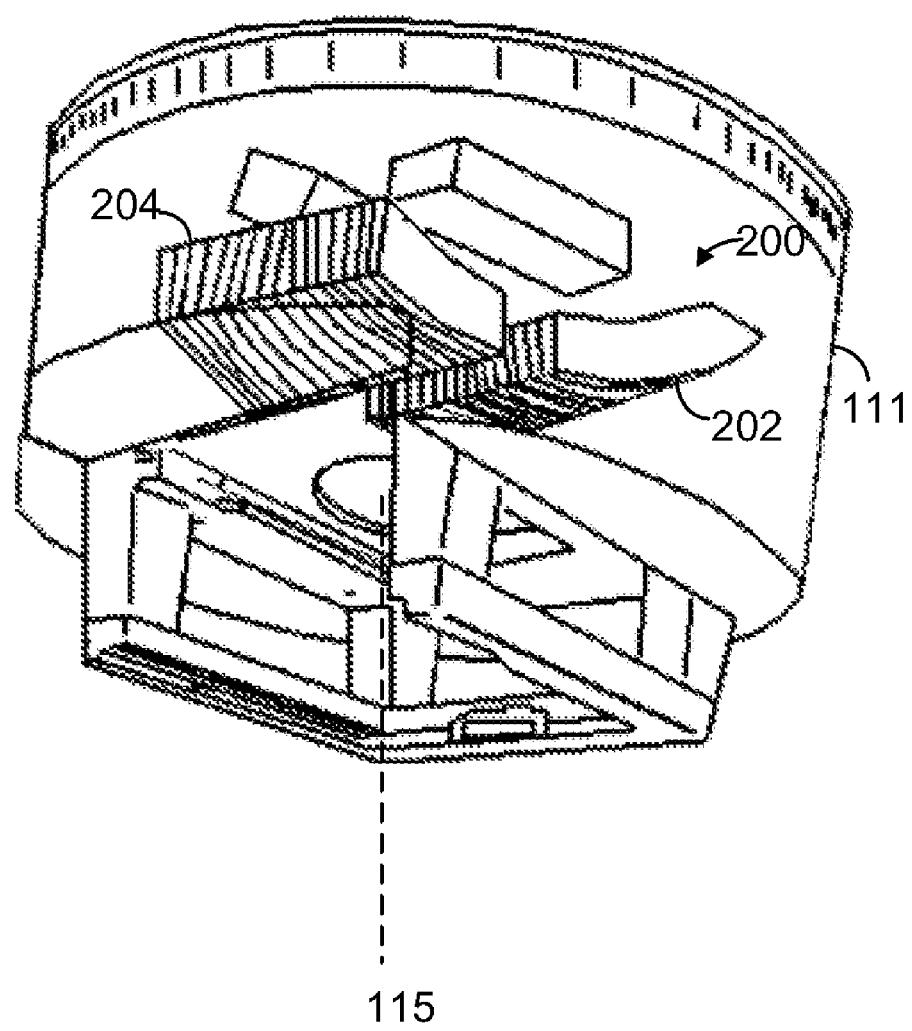
FIG. 2 is a perspective view of a portion of the radiation treatment room according to some embodiments.

FIG. 2 is perspective view of a portion of the treatment head 111, in accordance with some embodiments. Referring to FIG. 2, in some embodiments, collimator 200 includes multiple leafs 202, 204 for shaping the beam and for shielding sensitive surfaces from the beam.

Figure 3:
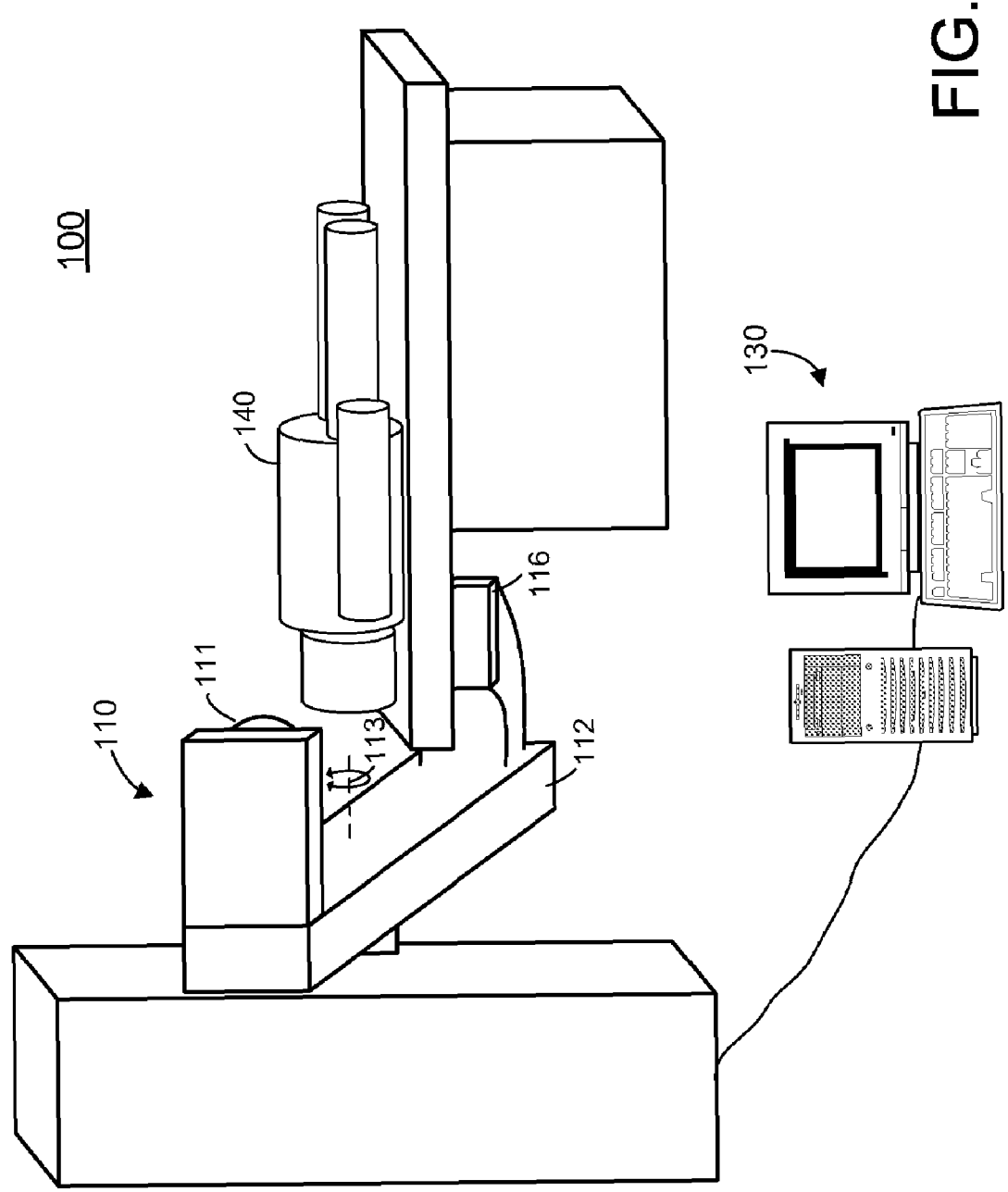
FIG. 3 is a perspective view of a radiation treatment room according to some embodiments.

FIG. 3 is a perspective view of the radiation treatment room 100 with the gantry 112 rotated, according to some embodiments.

Figure 4:
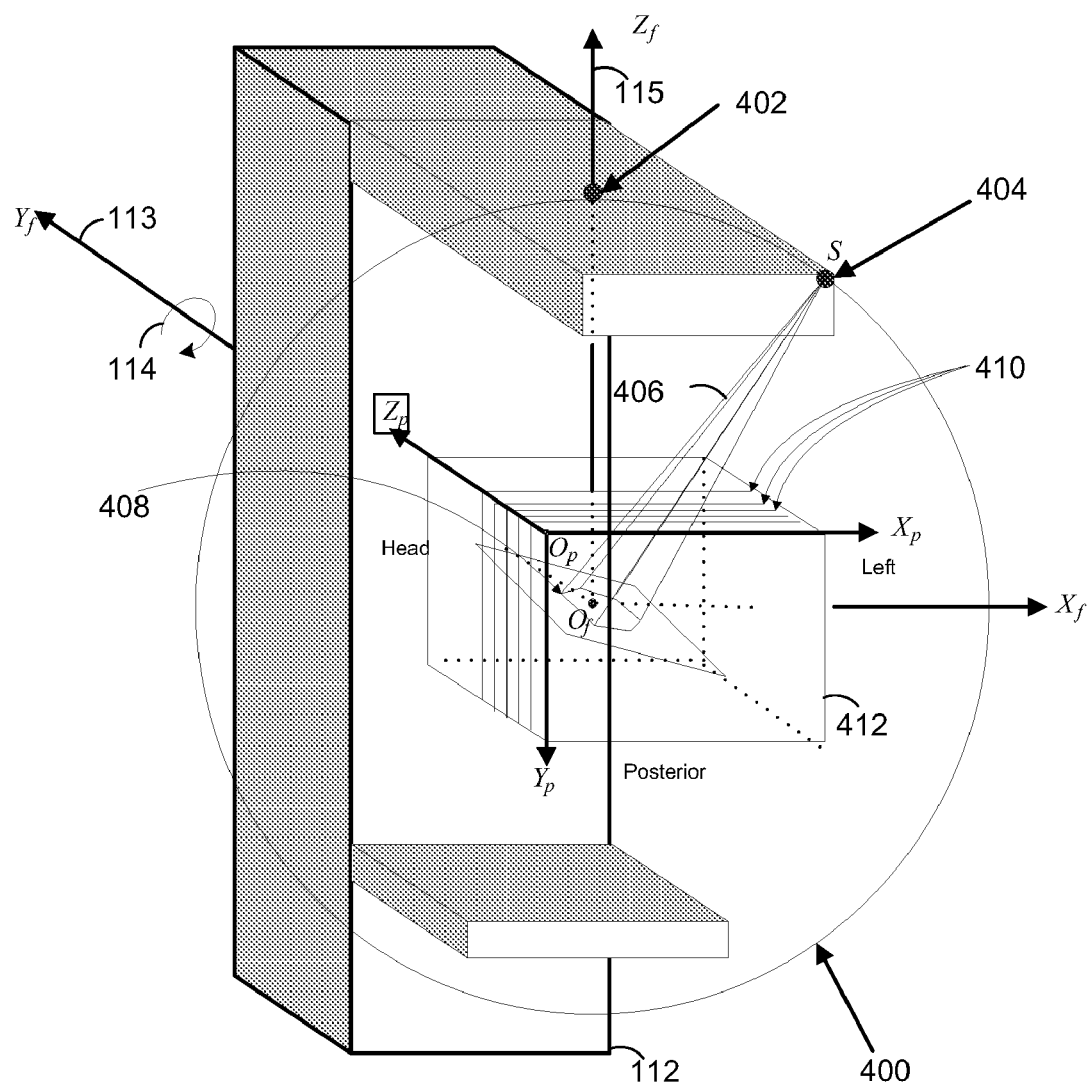
FIG. 4 is a perspective view of portion of a radiation treatment room and a patient volume according to some embodiments.

FIG. 4 is a perspective view of a portion of the treatment room 100 and a portion of the patient volume, in accordance with some embodiments.

Referring to FIG. 4, in accordance with some embodiments, the treatment room 100 may include a room co-ordinate system includes axes Xf, Yf (113), Zf (115). A patient co-ordinate system includes axes Xp, Yp, Zp.

In accordance with some embodiments, a circular source trajectory is indicated at 400. A source position when the gantry rotation is zero is indicated at 402. The source position when the gantry rotation is an angle other than zero is indicated at 404.

In accordance with some embodiments, a collimated segment of a beam 406 forms a pyramidal shape that intersects with the isocentric plane to form a beam's eye view (BEV) polygon 408. Image slices 410 may be acquired for and/or define a patient volume 412.

Figure 5:
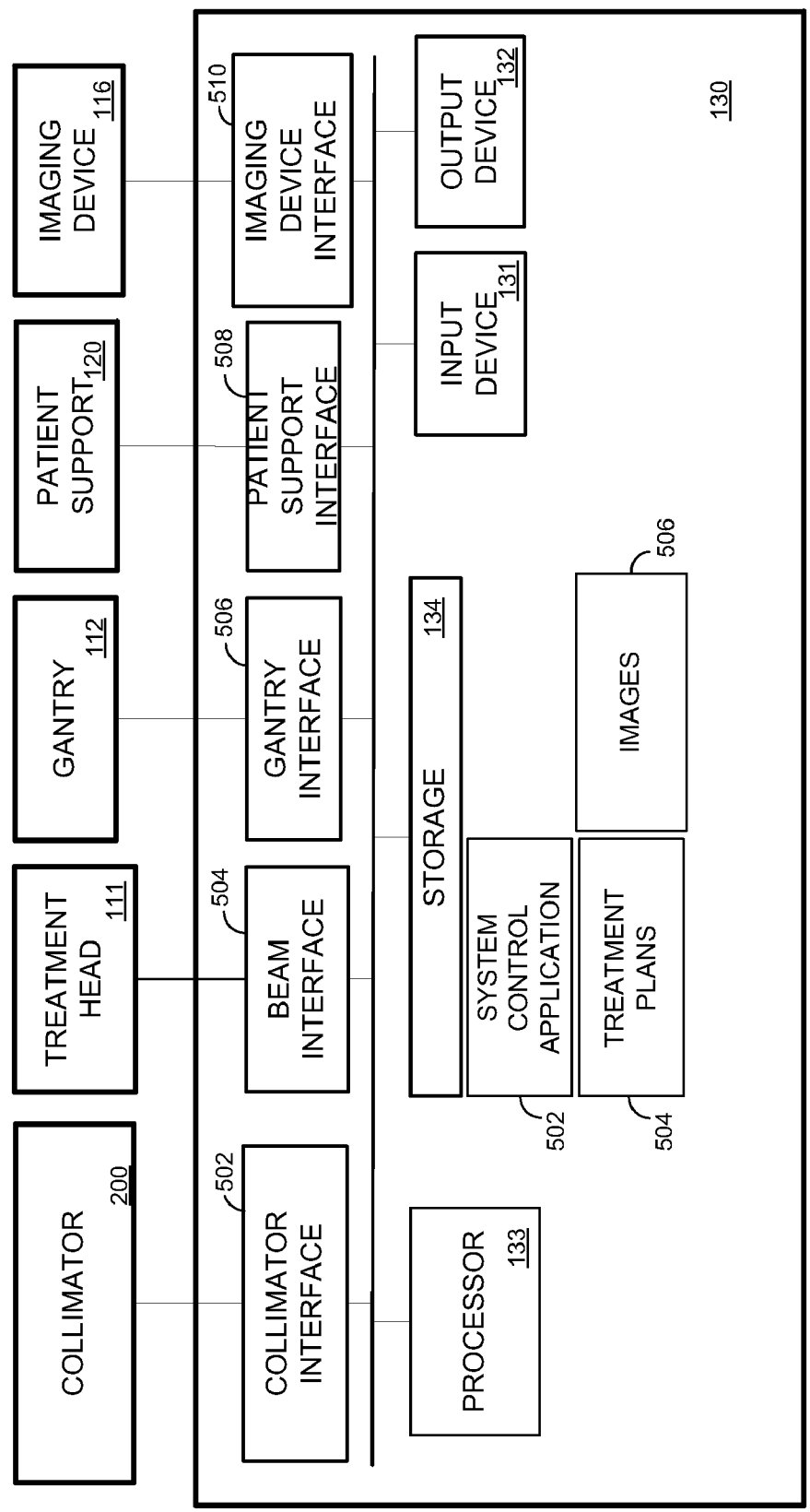
FIG. 5 is a block diagram of an internal architecture of radiation treatment devices according to some embodiments.

FIG. 5 is a block diagram of elements of treatment room 100, according to some embodiments. The illustrated elements may be implemented in any manner. In some embodiments, the elements are implemented by a combination of hardware, software and/or firmware.

Operator console 130 includes interfaces 502, 504, 506 and 508, 510 for interfacing with respective elements 200, 111, 112, 120 and 116 of treatment room 100. Each of the interfaces may comprise any suitable type of hardware and/or software interface, and may or may not be proprietary. Operator console 130 may control the various elements through the interfaces and based on instructions from processor 133.

The processor 133 may execute processor-executable process steps stored in storage 134 to provide operation according to some embodiments. These process steps may comprise system control application 512 to execute one of treatment plans 514. System control application 512 may, in some embodiments, be used to calibrate imaging device 116, to acquire projection images, to generate a three-dimensional image based on the projection images, and to determine a dose based on the three-dimensional image. Storage 134 may also comprise two and/or three-dimensional images 506 generated in conjunction with one or more process disclosed herein.

The processor 133 and the system control application 512 may, in some embodiments, be used to execute one or more portions of one or more of the processes disclosed herein.

A treatment system according to some embodiments may include less or more elements than those shown in FIGS. 1-5. In addition, embodiments are not limited to the devices and/or to the illustrated environment. For example, some embodiments include another type of image acquisition device to acquire projection images.

Figure 6:
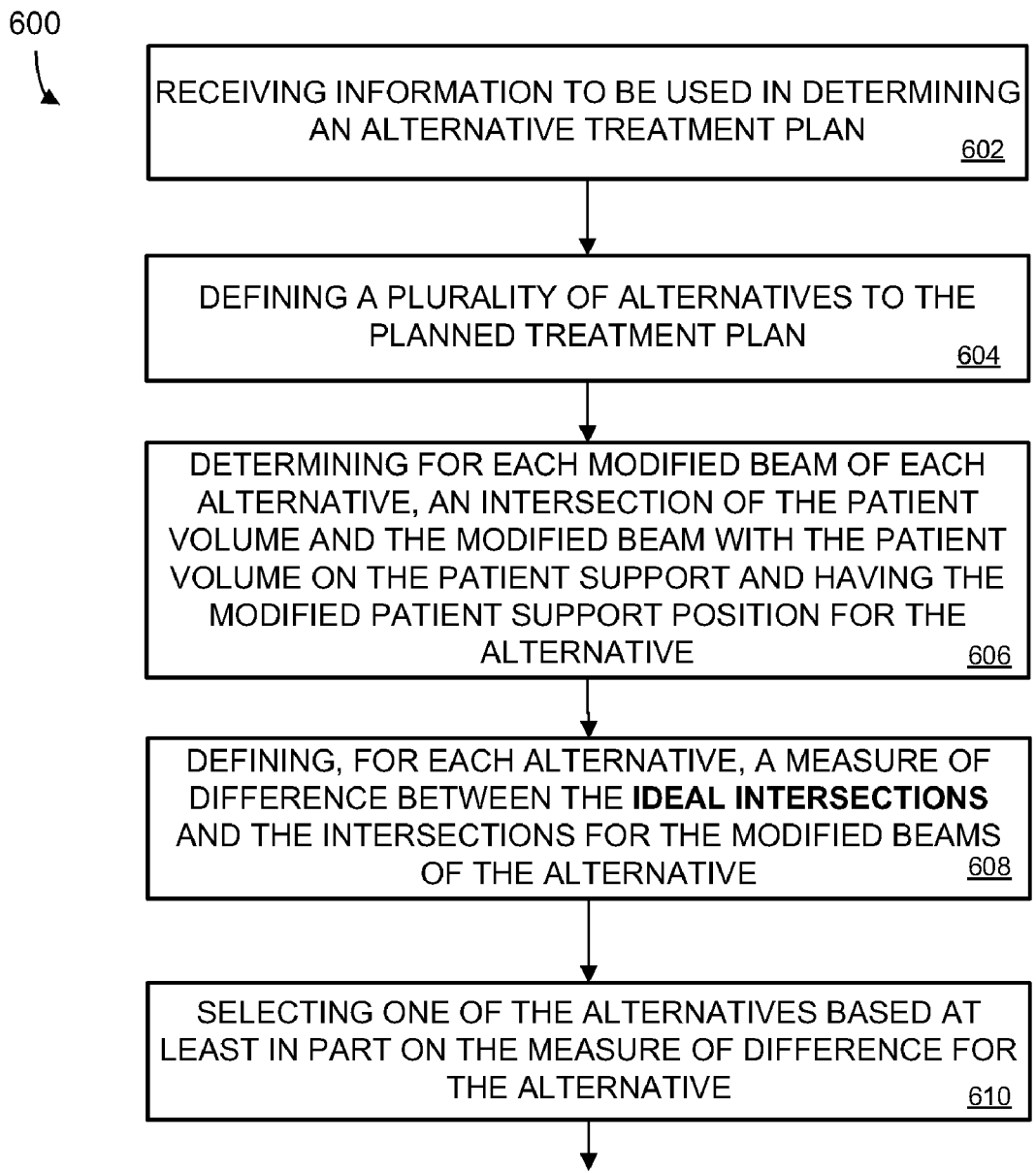
FIG. 6 is a flow diagram of a process according to some embodiments.

FIG. 6 is a flow diagram of a process 600 according to some embodiments. In some embodiments, the process 600 is used in determining an alternative treatment plan that accounts, at least in part, for changes in a position of a tumor or other target volume within a patient.

The process 600 is not limited to the order shown in the flow chart. Rather, embodiments of the process 600 may be performed in any order that is practicable. For that matter, unless stated otherwise, any process disclosed herein may be performed in any order that is practicable. Moreover, some embodiments may employ one or more portions of the process without one or more other portions of the process.

Referring to FIG. 6, at 602 the process may include receiving information to be used in determining an alternative treatment plan that accounts, at least in part, for changes in a position of a tumor or other target volume within a patient. In some embodiments, the information may include information indicative of (i) a treatment plan defining planned treatment beams, (ii) a patient volume relative to a reference (i.e., patient support, treatment room and/or other reference), (iii) ideal intersections of the planned treatment beams with the patient volume at the time the patient is to be treated (iv) any constraints that prevent achievement of the recommended repositioning using only the patient support and (v) allowable change to the gantry position (i.e., relative to a planned value) and allowable change to the collimator position (i.e., relative to a planned value).

In some embodiments, the information indicative of a patient volume relative to a reference comprises images of a patient volume placed on the patient support prior to treatment.

In some embodiments, the information includes a recommendation as to repositioning of the patient support to achieve six degree of freedom correction for the changes in the position of the tumor or other target volume within the patient.

In some embodiments, the ideal intersections of the planned treatment beams with the patient volume comprises ideal intersections of the planned treatment beams with the patient volume if the patient support is repositioned in accordance with the recommendation as to repositioning of the patient support to achieve six degree of freedom correction.

An ideal intersection is represented and described below with respect to FIG. 10.

In some embodiments, the recommended repositioning of the patient support includes a recommended translation along each of the three orthogonal axes (i.e., a recommended translation along an x axis, a recommended translation along a y axis and a recommended translation along a z axis) and a recommended rotation about each of the three orthogonal axes (i.e., a recommended rotation about the x axis, a recommended rotation about the y axis and a recommended rotation about the z axis) with the origin of the three orthogonal axes disposed at the isocenter of the radiotherapy device.

In some embodiments, each of the constraints that prevent achievement of the recommended repositioning using only the patient support may be defined directly. In some other embodiments, one or more of the constraints may be defined indirectly. For example, the information may define allowable changes to the patient support, which if less, in any dimension, than the recommended repositioning, indirectly defines one or more constraints that prevent achievement of the recommended repositioning using only the patient support.

Further in that regard, in accordance with some embodiments, and unless stated otherwise, any type of information described herein may be defined directly and/or indirectly.

In some embodiments, the constraints may be the same for all beams. In some other embodiments, there may be different constraints for different beams.

In some embodiments, the allowable changes may be the same for all beams. In some other embodiments, there may be different allowable changes for different beams.

At 604, the process may further include defining a plurality of alternatives to the planned treatment plan. In some embodiments, the alternatives are based at least in part on the constraints of the patient support, the allowable changes to the gantry position and the allowable changes to the collimator position. In some embodiments, each alternative defines (i) a modified patient support position, (ii) an amount of change to the gantry position for each planned treatment beam, (iii) an amount of change to the collimator position for each planned treatment beam and (iv) modified beams.

Any method(s) may be used to define the plurality of alternatives. In some embodiments, the alternatives are defined using an exhaustive search that increments uniformly through a multi-dimensional search space. In some other embodiments, a simulated annealing and/or an xyz plug in is employed.

In some embodiments, a plurality of alternatives are defined. One or more of the alternatives may avoid the need to change the patient support position for each beam. This may help to reduce the time needed to perform the treatment, as compared to the method described above for systems that use a patient support having only four degrees of freedom. One or more of the alternatives may avoid any change at all to the position of the patient support. This may help reduce the potential to disturb the position of the patient relative to the patient support.

A table of a subset of alternatives within a search space, in accordance with some embodiments, is described below with respect to FIG. 11.

The modified beams may be based at least in part on a respective one of the planned treatment beams, the change to the position of the gantry for the respective planned treatment beam and the change to the position of the collimator for the respective planned treatment beam.

The modified patient support position may include a translation for the patient support along one or more of the axes (i.e., a translation along an x axis, a translation along a y axis and/or a translation along a z axis) and a rotation for the patient support about one or more of the axes (i.e., a rotation about the x axis, a rotation about the y axis and/or a rotation about the z axis). In some embodiments, the modified patient support position may be the same for all alternatives. In some other embodiments, there may be a different modified patient support position for one or more of the alternatives. The modified patient support position may be defined directly and/or indirectly.

In some embodiments, the amount of change to the gantry position for a planned treatment beam may be defined relative to the non-rotated position for the gantry or relative to the planned position for the gantry for the planned treatment beam. In some embodiments, each alternative may define the same amount of change to the gantry position.

The amount of change to the collimator position for a planned treatment beam may be defined relative to the non-rotated position for the collimator or relative to the planned position for the collimator for the planned treatment beam. In some embodiments, each alternative may define the same amount of change to the collimator position.

At 606, the process may further include determining for each modified beam of each alternative, an intersection of the patient volume and the modified beam, with the patient volume placed on the patient support and having the modified patient support position for the alternative.

An intersection of a patient volume and a modified beam, in accordance with some embodiments, is represented and described below with respect to FIG. 10.

In some embodiments, there may be more than one intersection for a planned treatment beam. For example, some embodiments may use a particular planned treatment beam with different arrangements of collimator leafs (each arrangement of collimator leafs is sometimes referred to as a segment). In such embodiments, there may be a different intersection for each arrangement of collimator leafs (or segment).

At 608, the process may further include defining, for each alternative, a measure of difference between the ideal intersections and the intersections for the modified beams of the alternative.

A measure of difference between an ideal intersection and an intersection for a modified beam is represented and described below with respect to FIG. 10.

A process that may be used in defining the measure of difference is described below with respect to FIG. 7.

At 610, the process may further include selecting one of the alternatives based at least in part on the measure of difference for the alternative. In some embodiments, this includes selecting one of the alternatives for which the measure of difference between the ideal intersections and the intersections for the modified beams of the alternative is no greater than the measure of difference between the ideal intersections and the intersections for the modified beams of the other alternatives. In some embodiments, the selecting of one of the alternatives is performed by a processor. In some embodiments, the selecting of one of the alternatives is performed by a user and/or operator. In some embodiments, a processor receives an indication of the selection by the user and/or operator.

In some embodiments, the process may further include generating an ordered list of the alternatives based at least in part on the measure of difference for each of the alternatives. In some embodiments, this may help a user and/or operator select one of the alternatives. In some embodiments, an alternative having a measure of difference less than the other alternatives may be disposed first in the ordered list. In some embodiments, the ordered list is displayed on an output device. In some embodiments, the output device is the same as and/or similar to the output device 132 illustrated in FIG. 1 and/or FIG. 5. In some embodiments, a processor generates the ordered list and receives an indication of the selection by the user and/or operator.

The process 600 may be performed in any manner. In that regard, in some embodiments, one or more portions of any process disclosed herein may be performed by and/or using a processor. In some embodiments, such processor may be the same as and/or similar to the processor 133 illustrated in FIG. 1 and/or FIG. 5. In some embodiments, one or more portions of any process disclosed herein may be performed by and/or using one, some or all of the radiation treatment devices illustrated in FIG. 1 and/or FIG. 5.

As used herein, a processor may comprise any type of processor. For example, a processor may be programmable or non programmable, general purpose or special purpose, dedicated or non dedicated, distributed or non distributed, shared or not shared, and/or any combination thereof. A processor may include, but is not limited to, hardware, software, firmware, and/or any combination thereof. Hardware may include, but is not limited to off the shelf integrated circuits, custom integrated circuits and/or any combination thereof. Software may include, but is not limited to, instructions that are storable and/or stored on a computer readable medium, such as, for example, punch cards, paper tape, magnetic or optical disk, magnetic or optical tape, CD-ROM, DVD, RAM, EPROM, or ROM. A processor may employ continuous signals, periodically sampled signals, and/or any combination thereof. If a processor is distributed, two or more portions of the processor may communicate with one another through a communication link.

As used herein, a communication link may comprise any type of communication link, for example, but not limited to wired (e.g., conductors, fiber optic cables) or wireless (e.g., acoustic links, electromagnetic links or any combination thereof including, for example, but not limited to microwave links, satellite links, infrared links), and/or any combinations thereof. A communication link may be public or private, dedicated and/or shared (e.g., a network) and/or any combination thereof. A communication link may or may not be a permanent communication link. A communication link may support any type of information in any form, for example, but not limited to, analog and/or digital (e.g., a sequence of binary values, i.e. a bit string) signal(s) in serial and/or in parallel form. The information may or may not be divided into blocks. If divided into blocks, the amount of information in a block may be predetermined or determined dynamically, and/or may be fixed (e.g., uniform) or variable. A communication link may employ a protocol or combination of protocols including, for example, but not limited to the Internet Protocol.

Software that includes instructions to be executed by a processor to perform one or more portions of one or more processes may be stored by any processor readable medium, for example, punch cards, paper tape, magnetic or optical disk, magnetic or optical tape, CD-ROM, DVD, RAM, EPROM, or ROM. The processor readable medium may be and/or may be included in, an article of manufacture.

FIG. 7 is a flow diagram of a process 700 according to some embodiments. In some embodiments, one or more portions of the process 700 are used at 608 (FIG. 6) in defining a measure of difference between the ideal intersections and the intersections for the modified beams of an alternative.

Referring to FIG. 7, at 702, the process may include defining, for each modified beam of the alternative, a measure of difference between the intersection and a respective one of the ideal intersections. In some embodiments, the measure of difference between each intersection and the respective ideal intersection is based at least in part on a distance between a point defined by the intersection and a corresponding point defined by the respective ideal intersection.

A process that may be used at 702 is described below with respect to FIG. 8.

At 704, the process may further include defining a measure of difference between the ideal intersections and the intersections for the modified beams of the alternative based at least in part on the measure of difference between the intersection and the respective one of the ideal intersections for each modified beam of the alternative.

A process that may be used at 704 is described below with respect to FIG. 9.

FIG. 8 is a flow diagram of a process 800 according to some embodiments. In some embodiments, one or more portions of the process 800 are used at 702 (FIG. 7) in defining the measure of difference between an intersection and the respective ideal intersection.

Referring to FIG. 8, at 802, the process may include defining each intersection as a pyramid having a tip and a base. The base may comprise a polygonal shape having a plurality of corners.

At 804, the process may further include defining a distance between the tip of the intersection for the modified beam and the tip of the respective ideal intersection.

At 806, the process may further include defining for each corner of the intersection, a distance between the corner and a corresponding corner of the respective ideal intersection.

At 808, the process may further include defining a square of the distance between the tips.

At 810, the process may further include defining a square of the distance defined for each corner.

At 812, the process may further include defining the measure of difference between an intersection and the respective ideal intersection based at least in part on a sum of the square of the distance between the tips and the square of the distance defined for each corner of the polygon.

Figure 9:
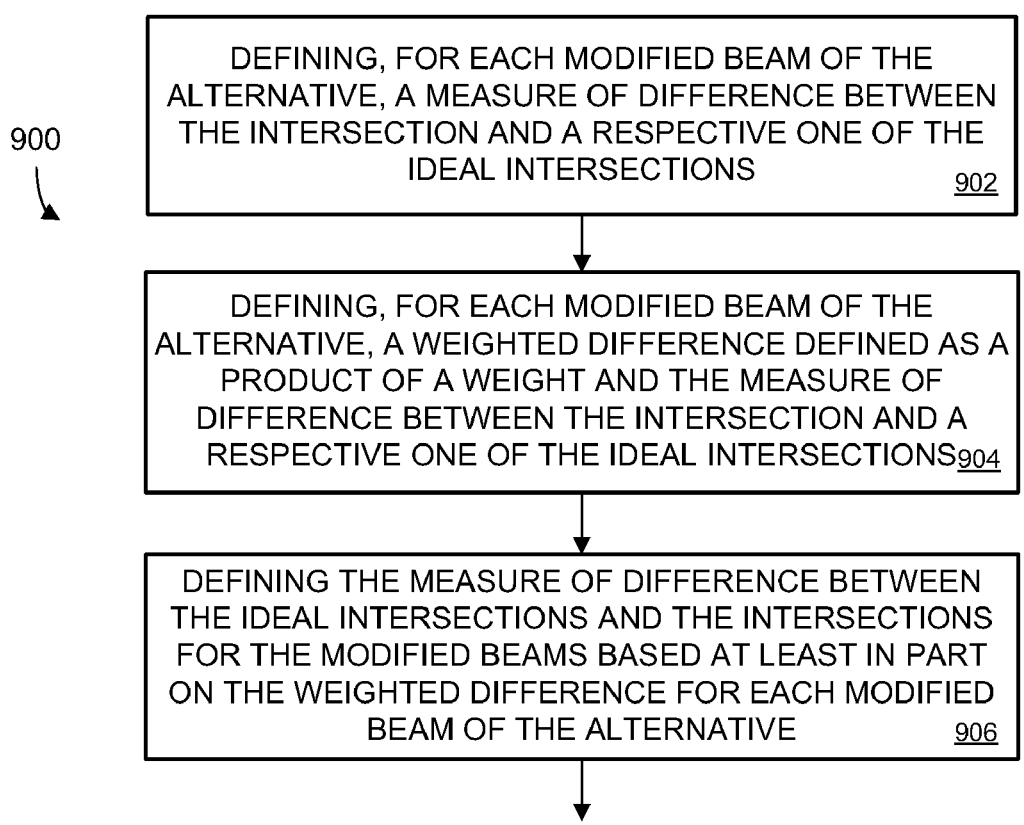
FIG. 9 is a flow diagram of a process according to some embodiments.
Figure 12A:
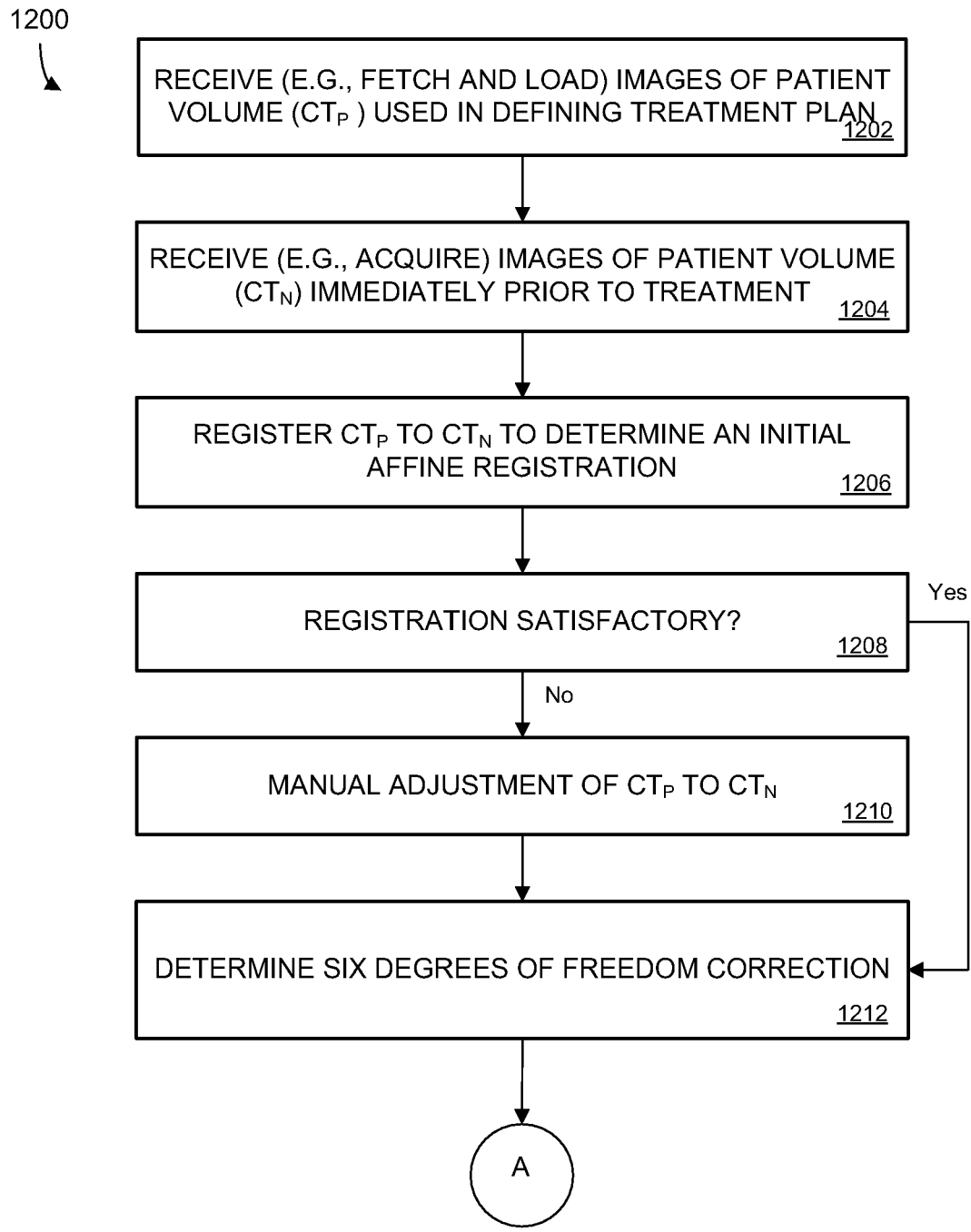
FIGS. 12A-12D are a flow diagram of a process according to some embodiments.
Figure 12B:
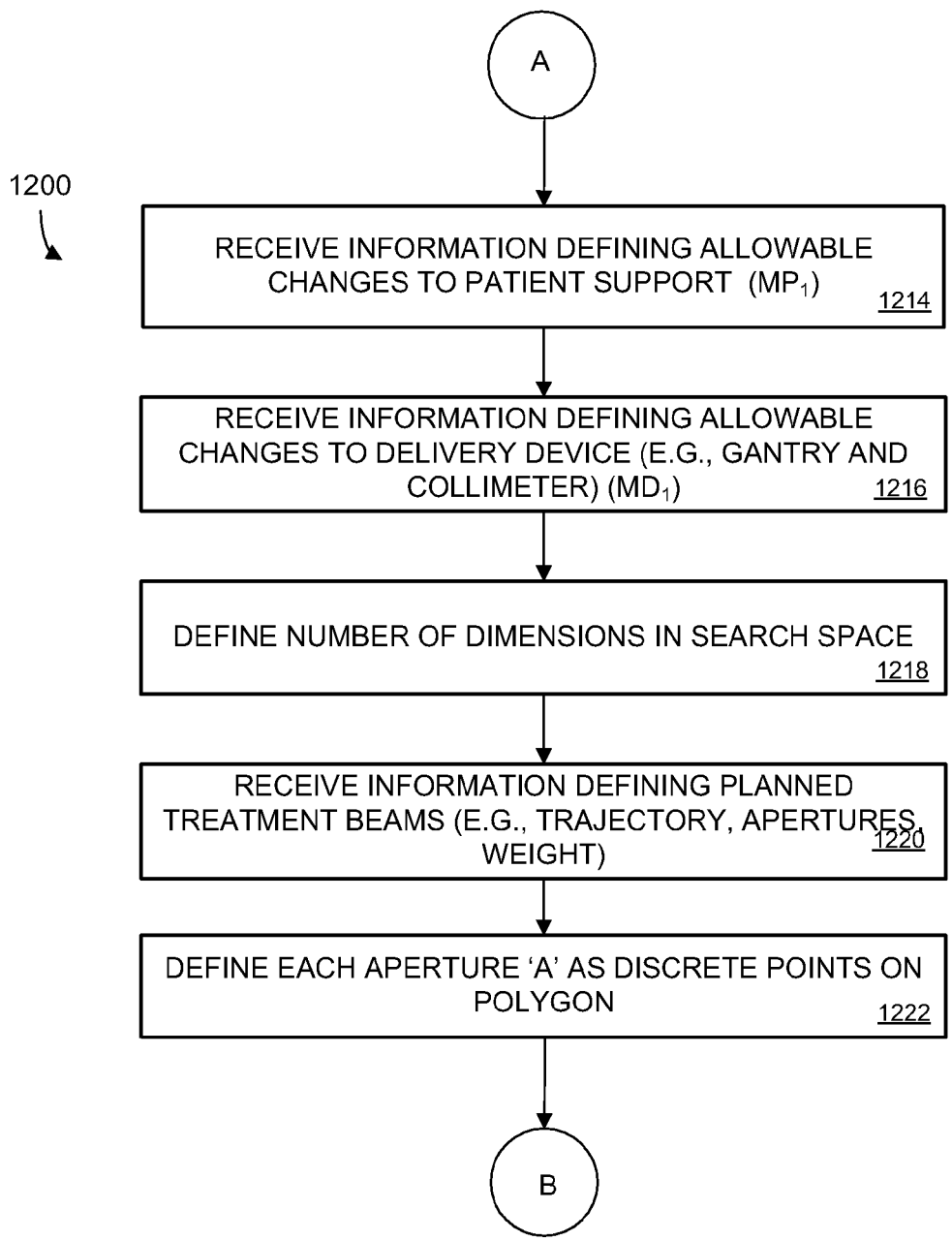
Figure 12C:
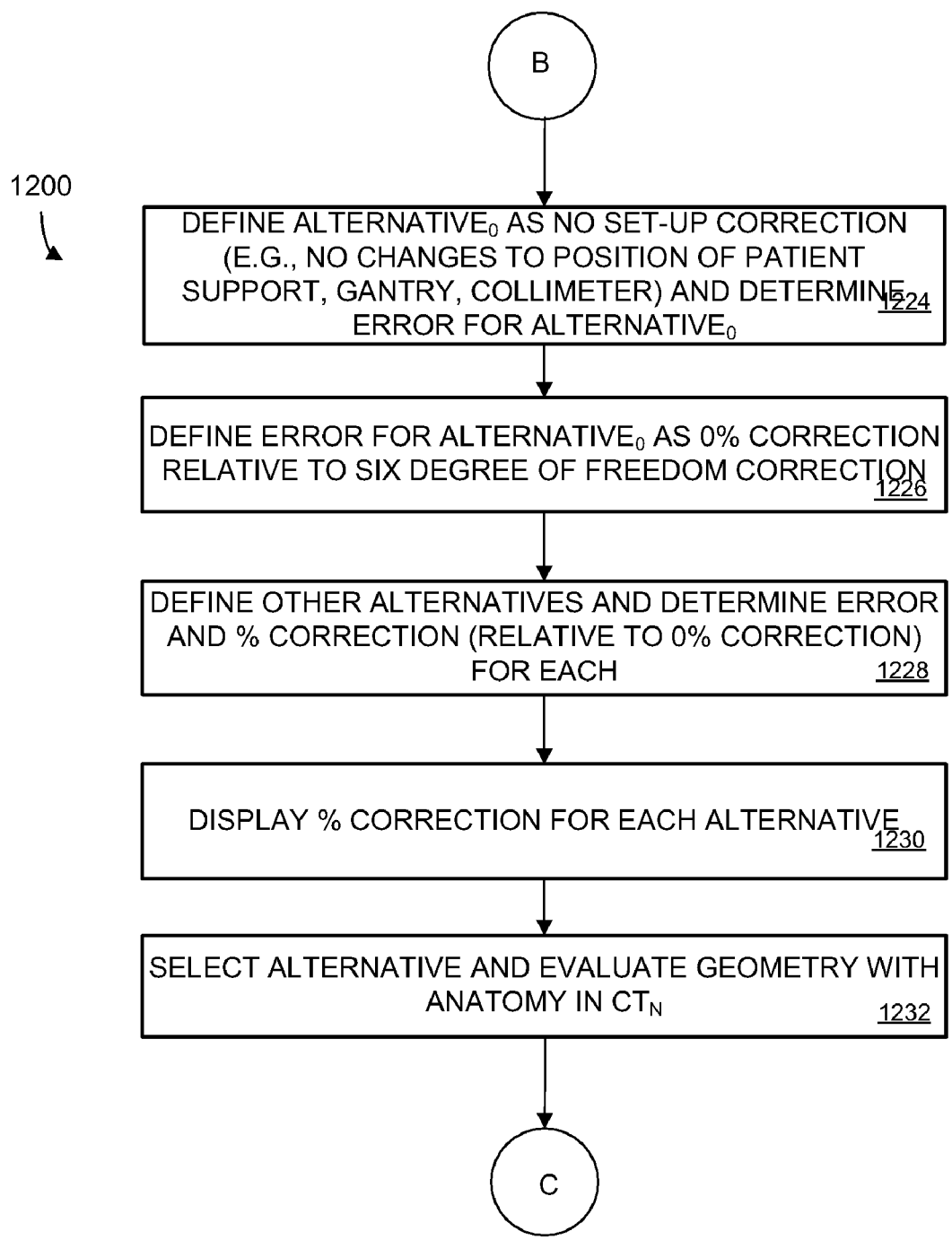
Figure 12D:
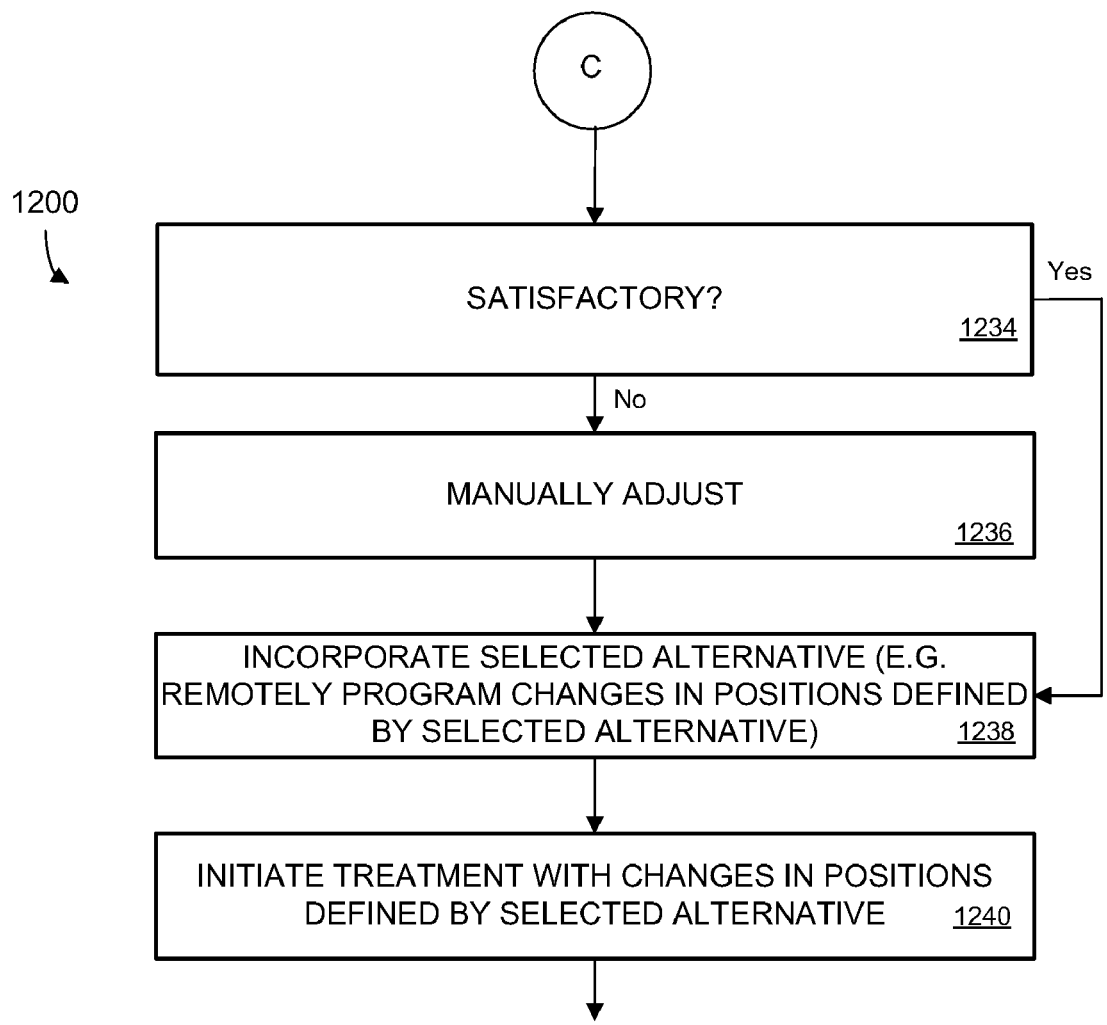

FIG. 9 is a flow diagram of a process 900 according to some embodiments. In some embodiments, one or more portions of the process 900 are used at 704 (FIG. 7) in defining the measure of difference between the ideal intersections and the intersections for the modified beams of the alternative.

Referring to FIG. 9, at 902, the process may include defining, for each modified beam of the alternative, a measure of difference between the intersection and a respective one of the ideal intersections.

At 904, the process may further include defining, for each modified beam of the alternative, a weighted difference defined as a product of a weight and the measure of difference between the intersection and a respective one of the ideal intersections. In some embodiments, the weight is based at least in part on a dosimetric strength of the modified beam relative to respective dosimetric strengths of the other modified beams of the alternative.

In accordance with some embodiments, the dosimetric strength of each modified beam may be defined in direct or indirect terms. In some embodiments, the dosimetric strength of each modified beam is defined in terms of the dose of each modified beam. In some other embodiments, the dosimetric strength of each modified beam is defined in terms of a field/segment area or any function of jaw settings etc. of each modified beam.

At 906, the process may further include defining the measure of difference between the ideal intersections and the intersections for the modified beams based at least in part on the weighted difference for each modified beam of the alternative. In some embodiments, the measure of difference between the ideal intersections and the intersections for the modified beams is based at least in part on the sum of the weighted difference for each modified beam of the alternative.

FIG. 10 is a diagrammatic representation 1000 of an ideal intersection and a modified intersection, in accordance with some embodiments.

Referring to FIG. 10, the diagrammatic representation 1000 includes first, second and third coordinate systems. The first coordinate system 1002 is an international electrotechnical commission (IEC) fixed (world) coordinate system. The second coordinate system 1004 is a patient coordinate system, shown with respect to the IEC fixed coordinate system, after a six degree of freedom patient set up correction using a robotic patient support. The third coordinate system 1006 is a patient coordinate system, with respect to the IEC fixed coordinate system, with an alternative set up correction that includes a modified patient support position made up of patient support translation and patient support rotation, a change in the gantry position and a change in the collimator position.

The representation further includes a planned beam (shown with a source at 1008) and an ideal intersection 1010 (shown expressed in the patient co-ordinate system 1004), in accordance with some embodiments. The planned beam is a beam that would result if the six degree of freedom patient set up correction is provided. The ideal intersection 1010 is the intersection of the planned beam and the patient volume. In accordance with some embodiments, the ideal intersection 1010 defines a pyramid having a tip (at the source 1008) and a base 1011 (in the isocentric plane). In accordance with some embodiments, the base 1011 is defined as a polygon having a plurality of corners, e.g., corners 1012-1026.

The representation further includes a modified beam (with a source at 1028) and a modified intersection 1030 (shown expressed in the patient co-ordinate system 1006), in accordance with some embodiments. The modified beam is a beam that would result if the alternative patient set up correction is provided. The modified intersection 1030 is the intersection of the modified beam and the patient volume. In accordance with some embodiments, the modified intersection 1030 defines a pyramid having a tip (at the source 1028) and a base 1031 (in the isocentric plane). In accordance with some embodiments, the base 1031 is defined as a polygon having a plurality of corners, e.g., corners 1032-1046.

In some embodiments, the arrangement of the collimator leafs for the planned beam is the same as the arrangement of the collimator leafs for the modified beam. Thus, the aperture may have the same shape for the planned beam and the modified beam.

A distance 1048 is shown between the tip of the modified intersection 1030 and the tip of the ideal intersection 1010.

A distance is also shown between each corner of the modified intersection 1030 and a corresponding corner of the ideal intersection 1010, i.e., a distance 1052 between corner 1032 of modified intersection 1030 and corner 1012 of ideal intersection 1010, a distance 1054 between corner 1034 of modified intersection 1030 and corner 1014 of ideal intersection 1010, a distance 1056 between corner 1036 of modified intersection 1030 and corner 1016 of ideal intersection 1010, a distance 1058 between corner 1038 of modified intersection 1030 and corner 1018 of ideal intersection 1010, a distance 1060 between corner 1040 of modified intersection 1030 and corner 1020 of ideal intersection 1010, a distance 1062 between corner 1042 of modified intersection 1030 and corner 1022 of ideal intersection 1010, a distance 1064 between corner 1044 of modified intersection 1030 and corner 1024 of ideal intersection 1010 and a distance 1066 between corner 1046 of modified intersection 1030 and corner 1026 of ideal intersection 1010.

In some embodiments, a measure of difference between the modified intersection 1030 and the ideal intersection 1010 may be defined as a sum of squares of distances 1048-1066.

In some embodiments, a measure of difference between the modified intersection 1030 and the ideal intersection 1010 may be defined as a product of a dosimetric strength and a sum of squares of distances 1048-1066.

In some embodiments, a measure of difference between the modified intersection 1030 and the ideal intersection 1010 may be defined as a product of the planned dose of the beam 1008 and the sum of squares of distances 1048-1066.

FIG. 11 is a table 1100 of a subset of the possible alternatives for a treatment plan having four beams, in accordance with some embodiments.

Referring to FIG. 11, the subset of the possible alternatives include a first alternative 1101, a second alternative 1102, a third alternative 1103, and so on. In accordance with some embodiments, each alternative defines five dimensions, i.e., a modified patient support position, an amount of change to the gantry position and an amount of change to the collimator position for each of the four beams. In accordance with some embodiments, the modified patient support position includes an amount of translation along an x-axis, an amount of translation along a y-axis, an amount of translation along a z-axis and an amount of rotation about one of the axes.

In accordance with some embodiments, the search space has a range of +/−5 mm for the translation along the x axis, a range of +/−5 mm for the translation along the y axis, a range of +/−5 mm for the translation along the z axis, +/−5 degrees for the change in the gantry position and +/−5 degrees for the change in the collimator position. FIG. 11 does not show the portion of the search space covering the negative portion of the ranges. In accordance with some embodiments, the increment amount is uniform and equal to +/−1.

In some embodiments, the number of possible alternatives will be equal to the total number of different possible combinations.

In some embodiments, the number of dimensions in the search space depends at least in part on the constraints that prevent achievement of the recommended repositioning using only the patient support.

In some embodiments, the number of dimensions are defined based on the allowable changes to the patient support (and/or other structures coupled to a patient), the allowable changes to the gantry position and the allowable changes to the collimator position. In some embodiments, the number of dimensions are defined as a sum of a degrees of freedom represented by the allowable changes to the patient support (and/or other structures coupled to a patient), a degrees of freedom represented by the allowable changes to the gantry position and a degrees of freedom represented by the allowable changes to the collimator position.

In some embodiments, a plurality of alternatives are defined. One or more of the alternatives may avoid the need to change the patient support position for each beam. This may help to reduce the time needed to perform the treatment, as compared to the method described above for systems that use a patient support having only four degrees of freedom. One or more of the alternatives may avoid any change at all to the position of the patient support. This may help reduce the potential to disturb the position of the patient relative to the patient support.

In some embodiments, the range for a dimension in the search space is selected based at least in part on the change in position of the tumor or other target volume in that dimension. In some embodiments, a greater change in position in a dimension may result in a greater range for that dimension in the search space.

FIGS. 12A-12D are a flow diagram of a process 1200 that may use and/or be used by processes 600-900, according to some embodiments.

Referring to FIGS. 12A-12D, at 1202, the process may include receiving images of a patient volume ($CT_P$) used in defining a treatment plan. In some embodiments, receiving the images comprises fetching the images from storage and loading the image into memory. In some embodiments, the images comprise computer tomography images acquired during planning.

At 1204, the process may further include receiving images of patient volume ($CT_N$) immediately prior to a treatment. In some embodiments, the images comprise computer tomography images.

At 1206, the process may further include registering the images of the patient volume ($CT_P$) to the images of patient volume ($CT_N$) to determine an initial affine registration. In some embodiments, this may be carried out using an affine registration service, intensity difference optimizers, cross correlation, and/or xyz plug in. In some embodiments, the initial affine registration defines a recommendation for setup correction. In some embodiments, the initial affine registration is in the form of a 4×4 matrix.

At 1208, the process may further include determining whether the registration is satisfactory. If the registration is not satisfactory, at 1210, the process may further include performing a manual six degree of freedom adjustment of the images of the patient volume ($CT_P$) to the images of patient volume ($CT_N$).

If the registration is satisfactory at 1208, then at 1212, the process may further include determining a six degree of freedom correction. If the initial affine registration is in the form of a 4×4 matrix, this may include decomposing the 4×4 matrix into the six degree of freedom correction.

At 1214, the process may further include receiving information defining allowable changes to a patient support.

At 1216, the process may further include receiving information defining allowable changes to a delivery device. In some embodiments the information defines allowable changes to a gantry position and allowable changes to a collimator position.

At 1218, the process may further include defining a number of dimensions for a search space. In some embodiments, the number of dimensions are defined based on the allowable changes to the patient support, the allowable changes to the gantry position and the allowable changes to the collimator position. In some embodiments, the number of dimensions are defined as a sum of a degrees of freedom represented by the allowable changes to the patient support, a degrees of freedom represented by the allowable changes to the gantry position and a degrees of freedom represented by the allowable changes to the collimator position.

In some embodiments, 1214-1218 are performed before and/or during 1202-1212.

At 1220, the process may further include receiving information that defines treatment beams of a treatment plan. In some embodiments, receiving may comprise fetching from storage and loading in memory. In some embodiments, the information includes an intensity, gantry position (angle), collimator position (angle), and position/shape of leafs that form the collimator, for each beam of the treatment plan.

At 1222, the process may further include defining each aperture 'A' as discrete points on a polygon.

In some embodiments, 1220-1222 are performed before and/or during 1202-1212 and/or 1214-1218.

At 1224, the process may further include defining alternative$_0$ as an alternative having no set-up correction, (e.g., no changes to the patient support position, no changes to the gantry position and no changes to the collimator position).

The process may further include determining an error associated with alternative$_0$. In some embodiments, this includes determining the error associated with each aperture of each gantry position.

The error associated with alternative$_0$ may thereafter be determined as a weighted sum of all the errors (i.e., a weighted sum of the error for each aperture of each gantry position). In some embodiments, the error for each aperture is weighted equally. In some other embodiments, the error for each aperture is weighted in accordance with the relative intensity of the intensity of the beam for that aperture.

In some embodiments, the processes 600-900 are used at 1224 in determining the error.

At 1226, the process may further include defining the error associated with alternative$_0$ as 0% correction.

At 1228, the process may further include defining other alternatives and determining an error and % correction for each of such alternatives.

Any method(s) may be used to define the plurality of alternatives. In some embodiments, the alternatives are defined using an exhaustive search that increments uniformly through a multi-dimensional search space. In some other embodiments, a simulated annealing and/or an xyz plug in is employed.

In some embodiments, a plurality of alternatives are defined. One or more of the alternatives may avoid the need to change the patient support position for each beam. This may help to reduce the time needed to perform the treatment, as compared to the method described above for systems that use a patient support having only four degrees of freedom. One or more of the alternatives may avoid any change at all to the position of the patient support. This may help reduce the potential to disturb the position of the patient relative to the patient support.

A table of some alternatives within a search space, in accordance with some embodiments, is described above with respect to FIG. 11.

In some embodiments, the error for each alternative is determined in a manner similar to that described above for alternative$_0$. In some embodiments, zero error is defined as 100% correction and the % correction associated with an alternative is determined as 100% multiplied by the difference between the error for the alternative and the error for alternative$_0$.

In some embodiments, the processes 600-900 are used at 1228 in determining the errors.

At 1230, the process may further include displaying the % correction for each alternative. The alternatives may also be displayed. In some embodiments, this may include displaying the alternatives and the % correction for each alternative in an ordered list. In some embodiments, the ordering of the alternatives in the ordered list is based at least in part on the % correction for the alternatives. In some embodiments, an alternative having a % correction greater than the other alternatives may be disposed first in the ordered list. In some embodiments, the ordered list is displayed on an output device. In some embodiments, the output device is the same as and/or similar to the output device 132 illustrated in FIG. 1 and/or FIG. 5.

At 1232, the process may further include selecting an alternative and evaluating the beam geometry of the alternative with the anatomy in the images of patient volume ($CT_N$). In some embodiments the beam geometry includes an intensity, gantry position (angle), collimator position (angle), and position/shape of leafs that form the collimator, for each beam of the alternative.

In some embodiments, the selecting of an alternative is performed by a processor. In some embodiments, the selecting of an alternative is performed by a user and/or operator.

At 1234, the process may further include determining whether the beam geometry of the alternative is satisfactory. If not satisfactory, at 1236, the method may further include performing a manual adjustment.

If the beam geometry is satisfactory at 1234, then at 1238, the process may further include incorporating the selected alternative into the treatment plan. In some embodiments, this may include remotely programming changes in the positions as defined by the selected alternative.

At 1240, the process may further include initiating treatment with the changes in positions defined the selected alternative.

As stated above, in some embodiments the process 1200 may use and/or be used by processes 600-900.

In some embodiments, one or more portions of processes 600-900 and/or 1200 may be performed after a patient has been placed on a patient support and is awaiting treatment.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A method comprising:
   receiving, in a processor, information indicative of (i) a treatment plan defining planned treatment beams, (ii) a patient volume relative to a reference, (iii) ideal intersections of the planned treatment beams with the patient volume at the time the patient is to be treated, (iv) any constraints that prevent achievement of the recommended repositioning using only the patient support, (v) an allowable change to a gantry position from a planned value and an allowable change to a collimator position from a planned value;
   defining, in the processor, a plurality of alternatives based at least in part on the information indicative of any constraints of the patient support and the information indicative of allowable movement of the gantry and collimator, each alternative defining a modified patient support position and modified beams, each modified beam being based at least in part on a respective one of the planned treatment beams, the change to the position of the gantry for the respective planned treatment beam and the change to the position of the collimator for the respective planned treatment beam;
   determining, in the processor, for each modified beam of each alternative, an intersection of the patient volume and the modified beam, with the patient volume positioned on the patient support and the patient support having the modified patient support position defined by the alternative; and
   defining, in the processor, for each alternative, a measure of difference between the ideal intersections and the intersections for the modified beams of the alternative.

2. The method of claim 1 wherein the modified patient support position defined by each alternative is the same.

3. The method of claim 1 wherein the amount of change to the gantry position defined by each alternative is the same.

4. The method of claim 1 wherein the amount of change to the collimator position defined by each alternative is the same.

5. The method of claim 1 wherein for each alternative, defining the measure of difference between the ideal intersections and the intersections for the modified beams of the alternative comprises:
   defining, for each modified beam of the alternative, a measure of difference between the intersection and a respective one of the ideal intersections; and
   defining the measure of difference between the ideal intersections and the intersections for the modified beams based at least in part on the measure of difference between the intersection and the respective one of the ideal intersections for each modified beam of the alternative.

6. The method of claim 5 wherein the measure of difference between each intersection and the respective ideal intersection is based at least in part on a distance between a point defined by the intersection and a corresponding point defined by the respective ideal intersection.

7. The method of claim 6 wherein each intersection for a modified beam defines a pyramid having a tip and a polygonal base, the tip defined by a source for the modified beam, the polygonal base having a plurality of corners, and wherein a measure of difference between each intersection and the respective ideal intersection is determined using a method comprising:
   defining a distance between the tip of the intersection and a tip of the respective ideal intersection;
   defining a square of the distance between the tips;
   defining for each corner of the polygonal base of the intersection, a distance between the corner and a corresponding corner of the respective ideal intersection;
   defining a square of the distance for each corner; and
   defining the measure of difference based at least in part on a sum of the square of the distance between the tips and the square of the distance defined for each corner of the polygon.

8. The method of claim 1 wherein for each alternative, defining the measure of difference between the ideal intersections and the intersections for the modified beams of the alternative comprises:
- defining, for each modified beam of the alternative, a measure of difference between the intersection and a respective one of the ideal intersections;
- defining, for each modified beam of the alternative, a weighted difference defined as a product of a weight and the measure of difference between the intersection and a respective one of the ideal intersections, wherein the weight is based at least in part on a dosimetric strength of the modified beam relative to respective dosimetric strengths of the other modified beams of the alternative; and
- defining the measure of difference between the ideal intersections and the intersections for the modified beams based at least in part on the weighted difference for each modified beam of the alternative.

9. The method of claim 8 wherein the measure of difference between the ideal intersections and the intersections for the modified beams is based at least in part on the sum of the weighted difference for each modified beam of the alternative.

10. The method of claim 1 further comprising selecting one alternative of the plurality of alternatives based at least in part on the measure of difference for the one alternative.

11. The method of claim 1 further comprising:
selecting one alternative of the plurality of alternatives for which the measure of difference between the ideal intersections and the intersections for the modified beams of the alternative is no greater than the measure of difference between the ideal intersections and the intersections for the modified beams of the other alternatives.

12. Apparatus comprising:
a processor to:
receive information indicative of (i) a treatment plan defining planned treatment beams, (ii) a patient volume relative to a reference, (iii) ideal intersections of the planned treatment beams with the patient volume at the time the patient is to be treated, (iv) any constraints that prevent achievement of the recommended repositioning using only the patient support, (v) an allowable change to a gantry position from a planned value and an allowable change to a collimator position from a planned value;
define a plurality of alternatives based at least in part on the information indicative of any constraints of the patient support and the information indicative of allowable movement of the gantry and collimator, each alternative defining a modified patient support position and modified beams, each modified beam being based at least in part on a respective one of the planned treatment beams, the change to the position of the gantry for the respective planned treatment beam and the change to the position of the collimator for the respective planned treatment beam;
determine for each modified beam of each alternative, an intersection of the patient volume and the modified beam, with the patient volume positioned on the patient support and the patient support having the modified patient support position defined by the alternative; and
define for each alternative, a measure of difference between the ideal intersections and the intersections for the modified beams of the alternative.

13. The apparatus of claim 12 wherein the modified patient support position defined by each alternative is the same.

14. The apparatus of claim 12 wherein the amount of change to the gantry position defined by each alternative is the same.

15. The apparatus of claim 12 wherein the amount of change to the collimator position defined by each alternative is the same.

16. The apparatus of claim 12 wherein the processor comprises a processor to:
- define, for each modified beam of the alternative, a measure of difference between the intersection and a respective one of the ideal intersections; and
- define the measure of difference between the ideal intersections and the intersections for the modified beams based at least in part on the measure of difference between the intersection and the respective one of the ideal intersections for each modified beam of the alternative.

17. The apparatus of claim 16 wherein the measure of difference between each intersection and the respective ideal intersection is based at least in part on a distance between a point defined by the intersection and a corresponding point defined by the respective ideal intersection.

18. The apparatus of claim 17 wherein each intersection for a modified beam defines a pyramid having a tip and a polygonal base, the tip defined by a source for the modified beam, the polygonal base having a plurality of corners, and wherein the processor comprises a processor to:
- define a distance between the tip of the intersection and a tip of the respective ideal intersection;
- define a square of the distance between the tips;
- define for each corner of the polygonal base of the intersection, a distance between the corner and a corresponding corner of the respective ideal intersection;
- define a square of the distance for each corner; and
- define the measure of difference based at least in part on a sum of the square of the distance between the tips and the square of the distance defined for each corner of the polygon.

19. The apparatus of claim 12 wherein the processor comprises a processor to:
- define, for each modified beam of the alternative, a measure of difference between the intersection and a respective one of the ideal intersections;
- define, for each modified beam of the alternative, a weighted difference defined as a product of a weight and the measure of difference between the intersection and a respective one of the ideal intersections, wherein the weight is based at least in part on a dosimetric strength of the modified beam relative to respective dosimetric strengths of the other modified beams of the alternative; and define the measure of difference between the ideal intersections and the intersections for the modified beams based at least in part on the weighted difference for each modified beam of the alternative.

20. The apparatus of claim 19 wherein the measure of difference between the ideal intersections and the intersections for the modified beams is based at least in part on the sum of the weighted difference for each modified beam of the alternative.

21. The apparatus of claim 12 wherein the processor comprises a processor to select one alternative of the plurality of alternatives based at least in part on the measure of difference for the one alternative.

22. The apparatus of claim 12 wherein the processor comprises a processor to select one alternative of the plurality of alternatives for which the measure of difference between the ideal intersections and the intersections for the modified beams of the alternative is no greater than the measure of difference between the ideal intersections and the intersections for the modified beams of the other alternatives.

23. An article comprising:
a processor readable storage medium having stored thereon instructions that if executed by a processor, result in the following:
receiving information indicative of (i) a treatment plan defining planned treatment beams, (ii) a patient volume relative to a reference, (iii) ideal intersections of the planned treatment beams with the patient volume at the time the patient is to be treated, (iv) any constraints that prevent achievement of the recommended repositioning using only the patient support, (v) an allowable change to a gantry position from a planned value and an allowable change to a collimator position from a planned value;
defining a plurality of alternatives based at least in part on the information indicative of any constraints of the patient support and the information indicative of allowable movement of the gantry and collimator, each alternative defining a modified patient support position and modified beams, each modified beam being based at least in part on a respective one of the planned treatment beams, the change to the position of the gantry for the respective planned treatment beam and the change to the position of the collimator for the respective planned treatment beam;
determining for each modified beam of each alternative, an intersection of the patient volume and the modified beam, with the patient volume positioned on the patient support and the patient support having the modified patient support position defined by the alternative; and
defining for each alternative, a measure of difference between the ideal intersections and the intersections for the modified beams of the alternative.

24. The article of claim 23 wherein the modified patient support position defined by each alternative is the same.

25. The article of claim 23 wherein the amount of change to the gantry position defined by each alternative is the same.

26. The article of claim 25 wherein the measure of difference between each intersection and the respective ideal intersection is based at least in part on a distance between a point defined by the intersection and a corresponding point defined by the respective ideal intersection.

27. The article of claim 26 wherein the measure of difference between the ideal intersections and the intersections for the modified beams is based at least in part on the sum of the weighted difference for each modified beam of the alternative.

28. The article of claim 23 wherein the amount of change to the collimator position defined by each alternative is the same.

29. The article of claim 28 wherein each intersection for a modified beam defines a pyramid having a tip and a polygonal base, the tip defined by a source for the modified beam, the polygonal base having a plurality of corners, and wherein a measure of difference between each intersection and the respective ideal intersection is determined using a article comprising:
defining a distance between the tip of the intersection and a tip of the respective ideal intersection;
defining a square of the distance between the tips;
defining for each corner of the polygonal base of the intersection, a distance between the corner and a corresponding corner of the respective ideal intersection;
defining a square of the distance for each corner; and
defining the measure of difference based at least in part on a sum of the square of the distance between the tips and the square of the distance defined for each corner of the polygon.

30. The article of claim 23 wherein for each alternative, defining the measure of difference between the ideal intersections and the intersections for the modified beams of the alternative comprises:
defining, for each modified beam of the alternative, a measure of difference between the intersection and a respective one of the ideal intersections; and
defining the measure of difference between the ideal intersections and the intersections for the modified beams based at least in part on the measure of difference between the intersection and the respective one of the ideal intersections for each modified beam of the alternative.

31. The article of claim 23 wherein for each alternative, defining the measure of difference between the ideal intersections and the intersections for the modified beams of the alternative comprises:
defining, for each modified beam of the alternative, a measure of difference between the intersection and a respective one of the ideal intersections;
defining, for each modified beam of the alternative, a weighted difference defined as a product of a weight and the measure of difference between the intersection and a respective one of the ideal intersections, wherein the weight is based at least in part on a dosimetric strength of the modified beam relative to respective dosimetric strengths of the other modified beams of the alternative; and defining the measure of difference between the ideal intersections and the intersections for the modified beams based at least in part on the weighted difference for each modified beam of the alternative.

32. The article of claim 23 wherein the method further comprises selecting one alternative of the plurality of alternatives based at least in part on the measure of difference for the one alternative.

33. The article of claim 23 wherein the method further comprises selecting one alternative of the plurality of alternatives for which the measure of difference between the ideal intersections and the intersections for the modified beams of the alternative is no greater than the measure of difference between the ideal intersections and the intersections for the modified beams of the other alternatives.

* * * * *